United States Patent [19]
Hiatt et al.

[11] Patent Number: 5,872,244
[45] Date of Patent: *Feb. 16, 1999

[54] 3' PROTECTED NUCLEOTIDES FOR ENZYME CATALYZED TEMPLATE-INDEPENDENT CREATION OF PHOSPHODIESTER BONDS

[75] Inventors: Andrew C. Hiatt, 660 Torrance St., San Diego, Calif. 92103; Floyd Rose, Del Mar, Calif.

[73] Assignees: Andrew C. Hiatt, San Diego; Floyd D. Rose, Del Mar, both of Calif.

[*] Notice: The term of this patent shall not extend beyond the expiration date of Pat. No. 5,763,594.

[21] Appl. No.: 486,535

[22] Filed: Jun. 7, 1995

Related U.S. Application Data

[63] Continuation-in-part of Ser. No. 300,484, Sep. 2, 1994.

[51] Int. Cl.$^6$ .................................................. C07H 19/00
[52] U.S. Cl. ...................... 536/26.26; 536/26.6; 536/26.7
[58] Field of Search ............................... 435/6; 536/25.3, 536/25.31, 25.32, 25.33, 25.34, 26.26, 26.6, 26.7

[56] References Cited

U.S. PATENT DOCUMENTS

| | | |
|---|---|---|
| 4,096,324 | 6/1978 | Kelly et al. . |
| 4,423,212 | 12/1983 | Skulnick . |
| 4,605,735 | 8/1986 | Miyoshi et al. . |
| 4,689,405 | 8/1987 | Frank et al. . |
| 4,719,176 | 1/1988 | Klotz . |
| 4,816,571 | 3/1989 | Andrus et al. . |
| 4,820,812 | 4/1989 | Miyoshi et al. . |
| 4,863,849 | 9/1989 | Melamede . |
| 4,876,335 | 10/1989 | Yamane et al. . |
| 4,948,882 | 8/1990 | Ruth . |
| 4,950,745 | 8/1990 | Ishido et al. . |
| 4,980,460 | 12/1990 | Molko et al. . |
| 5,003,059 | 3/1991 | Brennan . |
| 5,032,680 | 7/1991 | Kawai et al. . |
| 5,039,796 | 8/1991 | Engels et al. . |
| 5,047,524 | 9/1991 | Andrus et al. . |
| 5,091,519 | 2/1992 | Gruickshank ........................ 536/27.6 |
| 5,093,232 | 3/1992 | Urdea et al. . |
| 5,112,963 | 5/1992 | Pieles et al. . |
| 5,256,549 | 10/1993 | Urdea et al. . |
| 5,258,506 | 11/1993 | Urdea et al. . |
| 5,262,530 | 11/1993 | Andrus et al. . |
| 5,262,536 | 11/1993 | Hobbs, Jr. . |
| 5,264,563 | 11/1993 | Huse . |
| 5,264,566 | 11/1993 | Froehler et al. . |
| 5,268,266 | 12/1993 | Fritsch et al. . |
| 5,268,464 | 12/1993 | Brill . |
| 5,281,701 | 1/1994 | Vinayak . |
| 5,348,868 | 9/1994 | Reddy et al. . |
| 5,362,866 | 11/1994 | Arnold . |
| 5,367,066 | 11/1994 | Urdea et al. . |
| 5,380,833 | 1/1995 | Urdea . |
| 5,436,143 | 7/1995 | Hyman . |
| 5,652,099 | 7/1997 | Conrad . |

FOREIGN PATENT DOCUMENTS 55-38324  3/1980  Japan .

OTHER PUBLICATIONS

Hyman, Edward David, The Hyman Method: Oligonucleotide Synthesis and Plasmid Preparation, 1995.
Bollum, *Fed. Proc. Soc. Exp. Biol. Med.*, 17, 193 (1958).
Deng and Wu, *Meth. Enzymol.*, 100: 96–116 (1983).
Kaufmann et al., *Eur. J. Biochem*, 24:4–11 (1971).
Hinton and Gumport, *Nucleic Acid Res.*, 7:453–464 (1979).
Modak, *Biochemistry*, 17, 3116–3120 (1978).
England and Uhlenbeck, *Biochemistry*, vol. 17, 11:2069–2076 (1978).
Chang and Bollum, *Biochemistry*, vol. 10, 3:536–542 (1971).
Bennett et al., *Biochemistry*, vol. 12, 20:3956–3960 (1973).
Kossel and Roychoudrury, *Eur. J. Biochem*, 22:271–276 (1971).
Flugel et al., *Biochem. Biophys. Acta.*, 308:35–40 (1973).
Sarfati et al., *J. Biol. Chem.*, 265(31), 18902–18906 (1990).
Metzker et al., *Nucleic Acids Res.*, 22(20), 4259–4267 (1994).
Canard et al., *Proc. Nat'l. Acad. Sci. USA*, 92, 10859–10863 (Nov. 1995).

*Primary Examiner*—James O. Wilson
*Attorney, Agent, or Firm*—Lerner, David, Littenberg, Krumholz & Mentlik

[57] ABSTRACT

A method for the stepwise creation of phosphodiester bonds between desired nucleosides resulting in the synthesis of polynucleotides having a predetermined nucleotide sequence by preparing an initiation substrate containing a free and unmodified 3'-hydroxyl group; attaching a mononucleotide selected according to the order of the predetermined nucleotide sequence to the 3'-hydroxyl of the initiating substrate in a solution containing a catalytic amount of an enzyme capable of catalyzing the 5' to 3' phosphodiester linkage of the 5'-phosphate of the mononucleotide to the 3'-hydroxyl of the initiating substrate, wherein the mononucleotide contains a protected 3'-hydroxyl group, whereby the protected mononucleotide is covalently linked to the initiating substrate and further additions are hindered by the 3'-hydroxyl protecting group. Methods in which a mononucleotide immobilized on a solid support is added to a free polynucleotide chain are also disclosed.

6 Claims, 4 Drawing Sheets

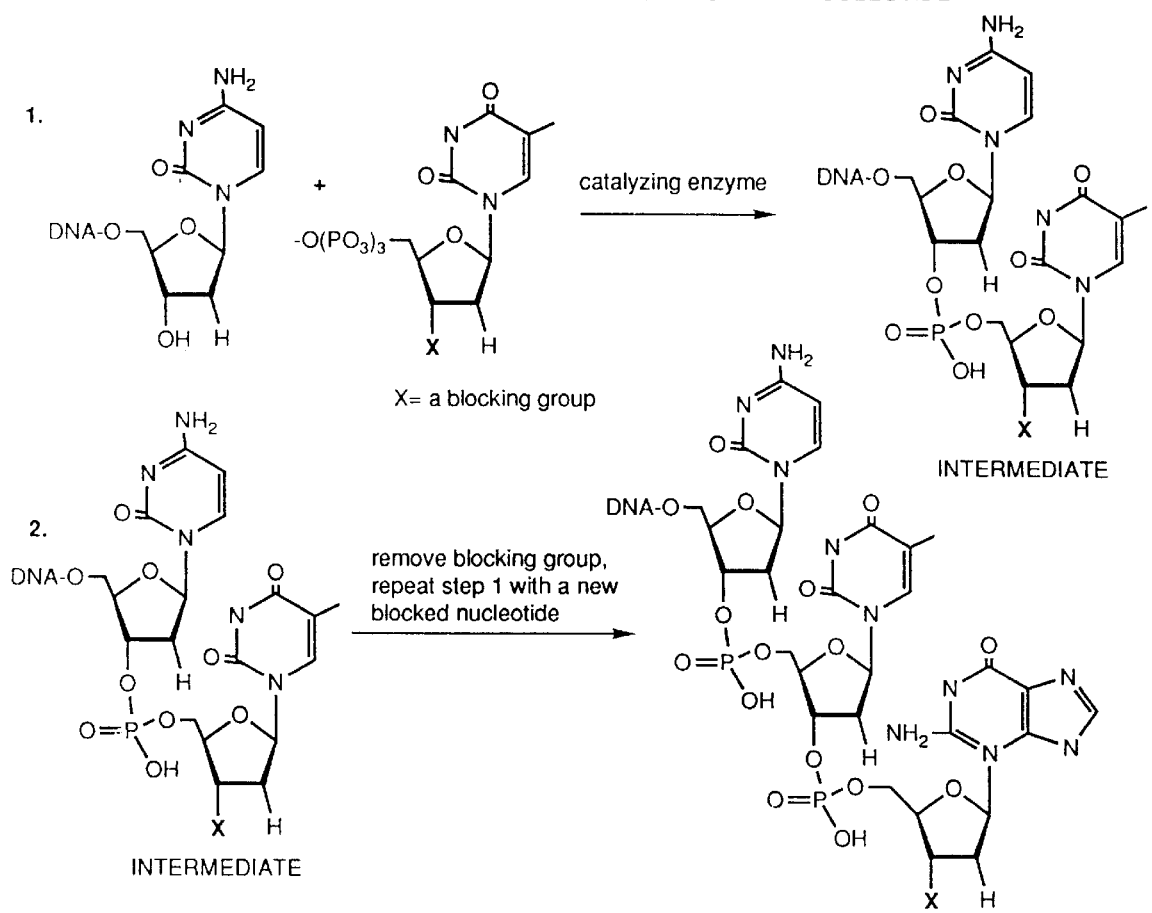
FIGURE 1. ENZYMATIC SYNTHESIS OF DNA USING A MODIFIED NUCLEOTIDE

FIGURE 2. EXAMPLE AND GENERAL STRUCTURE OF A BLOCKED NUCLEOTIDE
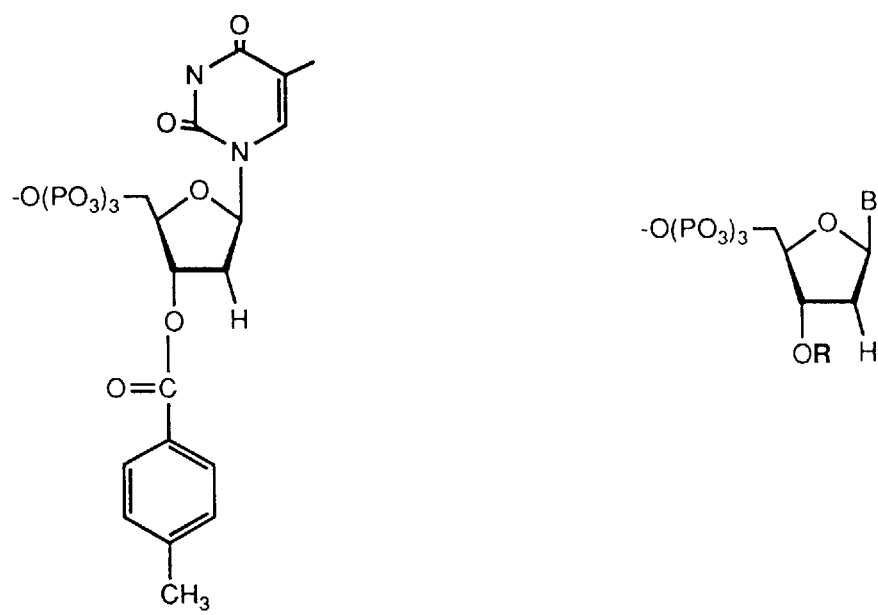
3'- TOLUIC ACID ESTER OF THYMIDINE 5'-TRIPHOSPHATE

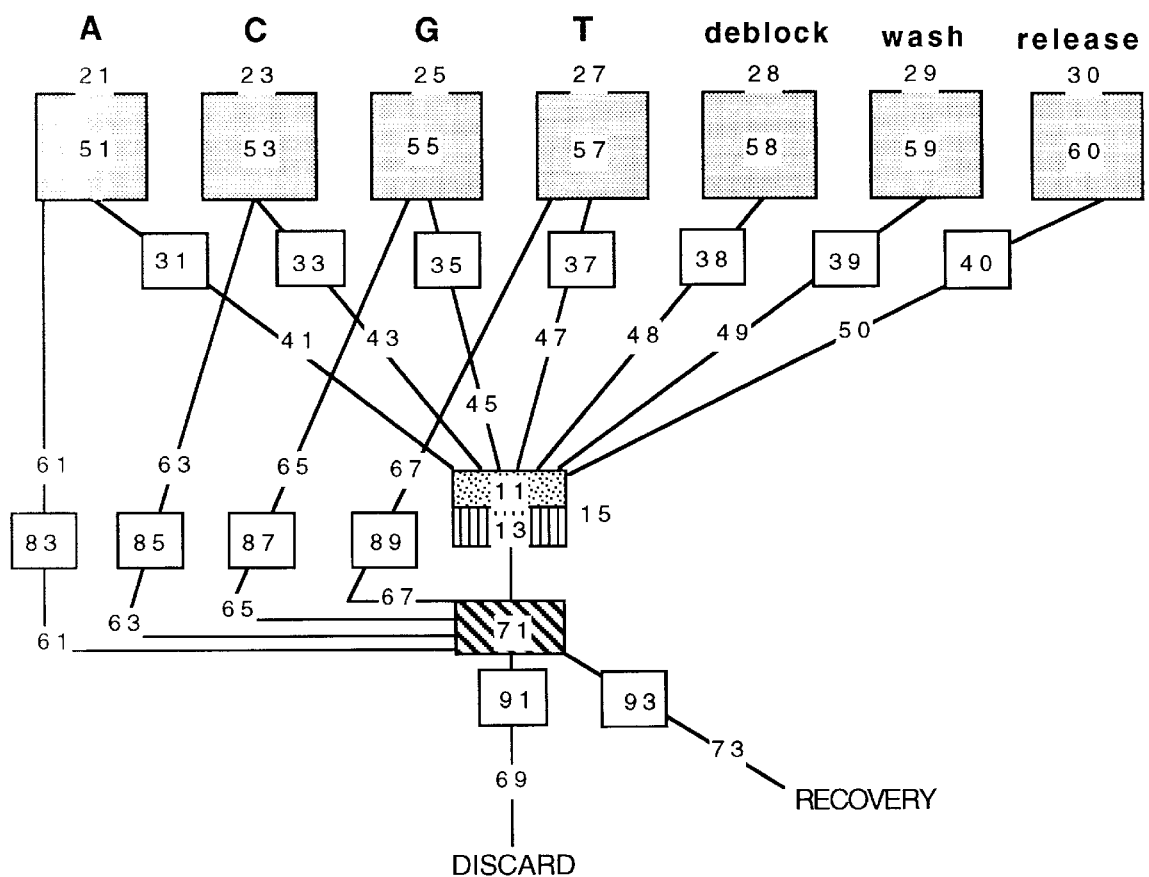
FIGURE 3. AUTOMATED PROCESS FOR THE ENZYMATIC SYNTHESIS OF DNA

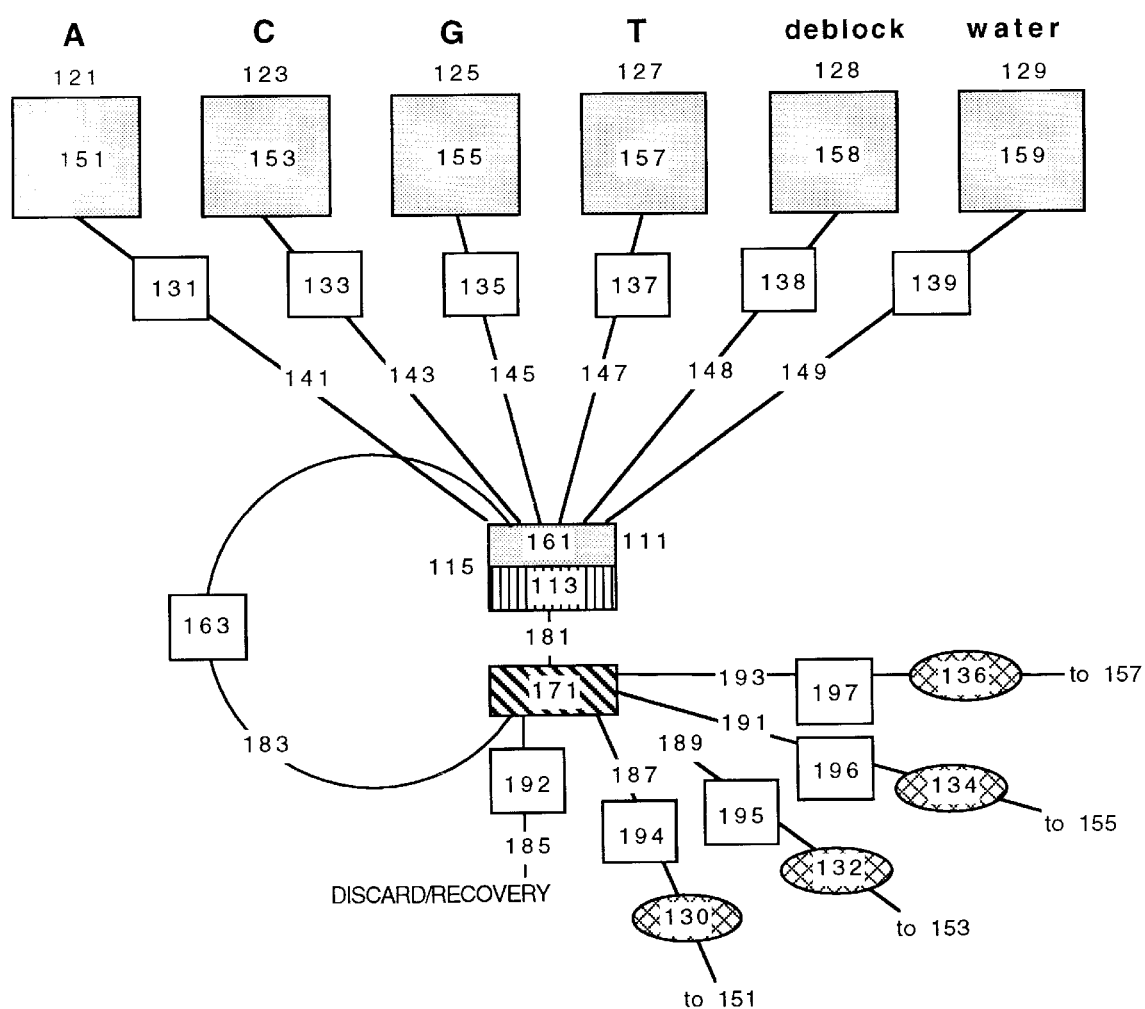
FIGURE 4. ALTERNATIVE AUTOMATED PROCESS FOR THE SYNTHESIS OF DNA 5,872,244

SEQUENCE LISTING ( 1 ) GENERAL INFORMATION:

( i i i ) NUMBER OF SEQUENCES: 8

( 2 ) INFORMATION FOR SEQ ID NO: 1:

( i ) SEQUENCE CHARACTERISTICS:
    ( A ) LENGTH: 12
    ( B ) TYPE: nucleic acid
    ( C ) STRANDEDNESS: single
    ( D ) TOPOLOGY: linear ( i x ) FEATURE:
    ( D ) OTHER INFORMATION: base number 12 is m7g ( x i ) SEQUENCE DESCRIPTION: SEQ ID NO: 1:

CCCCCCCCCC CG                                                                          12

( 2 ) INFORMATION FOR SEQ ID NO: 2:

( i ) SEQUENCE CHARACTERISTICS:
    ( A ) LENGTH: 19
    ( B ) TYPE: nucleic acid
    ( C ) STRANDEDNESS: single
    ( D ) TOPOLOGY: linear ( i i ) SEQUENCE DESCRIPTION: SEQ ID NO: 2:

CCCCCCCCCC CCCCCTGCA                                                                   19

( 2 ) INFORMATION FOR SEQ ID NO: 3:

( i ) SEQUENCE CHARACTERISTICS:
    ( A ) LENGTH: 20
    ( B ) TYPE: nucleic acid
    ( C ) STRANDEDNESS: single
    ( D ) TOPOLOGY: linear ( i i ) SEQUENCE DESCRIPTION: SEQ ID NO: 3:

CTGCAGGGGG GGGGGGGGGG                                                                  20

( 2 ) INFORMATION FOR SEQ ID NO: 4:

( i ) SEQUENCE CHARACTERISTICS:
    ( A ) LENGTH: 9
    ( B ) TYPE: nucleic acid
    ( C ) STRANDEDNESS: single
    ( D ) TOPOLOGY: linear ( i i ) SEQUENCE DESCRIPTION: SEQ ID NO: 4:

CCCCCCCCC                                                                               9

( 2 ) INFORMATION FOR SEQ ID NO: 5:

( i ) SEQUENCE CHARACTERISTICS:
    ( A ) LENGTH: 9
    ( B ) TYPE: nucleic acid
    ( C ) STRANDEDNESS: single
    ( D ) TOPOLOGY: linear ( i i ) SEQUENCE DESCRIPTION: SEQ ID NO: 5:

GGGGGGGGG                                                                               9

( 2 ) INFORMATION FOR SEQ ID NO: 6:

( i ) SEQUENCE CHARACTERISTICS:
    ( A ) LENGTH: 5

```
            (B) TYPE: nucleic acid
            (C) STRANDEDNESS: single
            (D) TOPOLOGY: linear (i i) SEQUENCE DESCRIPTION: SEQ ID NO: 6:

CTGCA                                                                5

(2) INFORMATION FOR SEQ ID NO: 7:

(i) SEQUENCE CHARACTERISTICS:
            (A) LENGTH: 9
            (B) TYPE: nucleic acid
            (C) STRANDEDNESS: single
            (D) TOPOLOGY: linear (i i) SEQUENCE DESCRIPTION: SEQ ID NO: 7:

CTGCATGCA                                                            9

(2) INFORMATION FOR SEQ ID NO: 8:

(i) SEQUENCE CHARACTERISTICS:
            (A) LENGTH: 10
            (B) TYPE: nucleic acid
            (C) STRANDEDNESS: single
            (D) TOPOLOGY: linear (i i) SEQUENCE DESCRIPTION: SEQ ID NO: 8:

CTGCATGCAG                                                          10
```

3' PROTECTED NUCLEOTIDES FOR ENZYME CATALYZED TEMPLATE-INDEPENDENT CREATION OF PHOSPHODIESTER BONDS

RELATED APPLICATIONS

This Application is a continuation-in-part of U.S. patent application Ser. No. 08/300,484 filed Sep. 2, 1994.

TECHNICAL FIELD

This invention relates to the synthesis of oligonucleotides and other nucleic acid polymers using template independent enzymes.

BACKGROUND OF THE INVENTION

Oligonucleotides are presently synthesized in vitro using organic synthesis methods. These methods include the phophoramidite method described in Adams et al., *J. Amer. Chem. Soc.*, 105:661 (1983) and Froehler et al., *Tetrahedron Lett.*, 24:3171 (1983) and the phosphotriester method described in German Offenlegungsshrift 264432. Other organic synthesis methods include those described by Froehler et al., U.S. Pat. No. 5,264,566 in which H-phosphonates are used to produce oligonucleotides.

The phosphoramidite method of phosphodiester bond formation and oligonucleotide synthesis represents the current state of the art employed by most laboratories for the coupling of desired nucleotides without the use of a template. In this method, the coupling reaction is initiated by a nucleoside attached to a solid support.

The 5'-hydroxyl group of the immobilized nucleoside is free for coupling with the second nucleoside of the chain to be assembled. Since the growing oligonucleotide chain projects a 5'-hydroxyl available for reaction with a mononucleotide, the direction of synthesis if referred to as 3' to 5'.

Each successive mononucleotide to be added to the growing oligonucleotide chain contains a 3'-phosphoramidate moiety which reacts with the 5'-hydroxyl group of the support-bound nucleotide to form a 5' to 3' internucleotide phosphodiester bond. The 5'-hydroxyl group of the incoming mononucleotide is protected, usually by a trityl group, in order to prevent the uncontrolled polymerization of the nucleosides. After each incoming nucleoside is added, the protected 5'-hydroxyl group is deprotected, so that it is available for reaction with the next incoming nucleoside having a 3'-phosphoramidite group and a protected 5'-hydroxyl. This is followed by deprotection and addition of the next incoming nucleotide, and so forth.

Between each nucleoside addition step, unreacted chains which fail to participate in phosphodiester bond formation with the desired nucleoside are chemically "capped" to prevent their further elongation. This usually involves chemical acetylation.

This method and the other currently used organic methods while widely accepted require large amounts of costly monomers that require complex organic synthesis schemes to produce. In addition, these methods are complex in that the phosphoramidite method requires an oxidation step after each condensation reaction. The phosphotriester method requires that the subpopulation of oligonucleotides that have not had a monomer added in a particular cycle be capped in a separate reaction to prevent further chain elongation of these oligonucleotides.

Other drawbacks of virtually all chemical methods of phosphodiester bond formation, is that the reaction must be performed in organic solvents and in the absence of water. Many of these organic solvents are toxic or otherwise hazardous. Another drawback to chemical synthesis is that it is at best 98 percent efficient at each cycle. In other words, following each nucleotide addition, at least 2 percent of the growing oligonucleotide chains are capped, resulting in a yield loss. The total yield loss for the nucleotide chain being synthesized thus increases with each nucleotide added to the sequence.

For example, assuming a yield of 98 percent per nucleotide addition, the synthesis of a polynucleotide consisting of 70 mononucleotides would experience a yield loss of nearly 75 percent. Furthermore, the object nucleotide chain would require isolation from a reaction mixture of polynucleotides, nearly 75 percent of which consist of capped oligonucleotides ranging between 1 and 69 nucleotides in length.

This inherent inefficiency in chemical synthesis of oligonucleotides ultimately limits the length of oligonucleotide that can be efficiently produced to oligonucleotides having 50 nucleic acid residues or less.

A need exists for a method which improves the efficiency of phosphodiester bond formation and which could ultimately be capable of producing shorter chain oligonucleotides in higher yields and longer chain polynucleotides in acceptable yields. In addition, a need exists for a polynucleotide synthesis system which is compatible with pre-existing polynucleotides, such as vector DNAs, so that desired polynucleotide sequences can readily be added on to the pre-existing sequences. Chemical coupling by the phosphoramidite method is not compatible with "add-on" synthesis to pre-existing polynucleotides. Enzyme catalyzed phosphodiester bond formation, however, can be performed in an aqueous environment utilizing either single or double stranded oligo- or polynucleotides to initiate the reaction. These reaction conditions also greatly minimize the use of toxic and hazardous materials.

The 3' to 5' direction of synthesis inherent to the phosphoramidite method of phosphodiester bond formation cannot be enzyme catalyzed. All known enzymes capable of catalyzing the formation of phosphodiester bonds do so in the 5' to 3' direction since the growing polynucleotide strand always projects a 3'-hydroxyl available for attachment of the next nucleoside.

There are many enzymes capable of catalyzing the formation of phosphodiester bonds. One class of such enzymes, the polymerases, are largely template dependent in that they add a complementary nucleotide to the 3' hydroxyl of the growing strand of a double stranded polynucleotide. However, some polymerases are template independent and primarily catalyze the formation of single stranded nucleotide polymers. Another class of enzyme, the ligases, are template independent and form a phosphodiester bond between two polynucleotides or between a polynucleotide and a mononucleotide.

Addition of single nucleotides to DNA fragments, catalyzed by deoxynucleotidyl terminal transferase (TdTase), has previously been described by Deng and Wu, *Meth. Enzymol.*, 100:96–116, 1983. These reaction conditions did not involve transient protection of the 3'-hydroxyl nor were they intended to be used for the sequential creation of phosphodiester bonds to synthesize a predetermined nucleotide sequence. The presence of unprotected 3'-hydroxyls resulted in a highly heterogeneous population of reaction products.

Similarly, prior attempts to catalyze synthesis of very short pieces of RNA or DNA using protected nucleotide monophosphates or diphosphates resulted in unacceptably low levels of the desired phosphodiester bond formation or required excessive amounts of enzyme to achieve acceptable efficiencies. These problems were largely due to unavoidable heterogeneity of the mononucleotide building blocks or to the very high turnover number of the enzyme, necessitating extremely long incubation times (see, for example, Hinton and Gumport, *Nucleic Acids Res.* 7:453–464, 1979; Kaufman et al., *Eur. J. Biochem.,* 24: 4–11, 1971). These experiments were limited to 5'-monophosphates and diphosphates. No attempts have been made to catalyze controlled DNA synthesis using 5'-triphosphates protected at the 3' position.

Enzyme catalyzed creation of a single phosphodiester bond between the free $3^1$-hydroxyl group of an oligonucleotide chain and the 5'-phosphate of a mononucleotide requires protection of the 3'-hydroxyl of the mononucleotide in order to prevent multiple phosphodiester bond formations and hence repeated mononucleotide additions. Protection of the 3'-hydroxyl of the mononucleotide ideally involves a transient blocking group which can readily be removed in order to allow subsequent reactions. Flugel et al., *Biochem. Biophys. Acta.* 308:35–40, 1973, report that nucleoside triphosphates with blocked 3'-hydroxyl groups cannot be prepared directly. This lack of 3' blocked triphosphates necessitated previous processes to utilize lower energy and thus more inefficient 3' blocked monophosphates and diposphates. Synthetic techniques to create 3' block triphosphates would be highly desirable, because this could enable stepwise enzyme catalyzed phosphodiester bond formation leading to polynucleotide synthesis.

These prior attempts at synthesizing oligonucleotides using a template independent polymerase were extremely inefficient resulting in the production of very short oligonucleotides. The inefficiency of these methods made these methods useless for practical synthesis of oligonucleotides.

The present invention allows the creation of phosphodiester bonds between nucleotides using a template independent polymerase to create oligonucleotides having a predetermined sequence. This enzyme catalysis can vastly improve the efficiency of phosphodiester bond formation between desired nucleotides compared to current techniques of chemical coupling and can be carried out in the presence of other biological molecules such as pre-existing sequences of single or double stranded DNA as well as other types of enzymes. In addition, the very high specificity inherent to enzyme catalysis allows only coupling of a 5'-phosphate to a 3'-hydroxyl. The coupling of two mononucleosides, as well as various other side reactions inherent to chemical coupling techniques, simply do not occur.

A further advantage of the present invention is realized by using 3' blocked triphosphates having high energy phosphate bonds which an enzyme can utilize to drive the reaction to greater completion level than when other monophosphates and diphosphates are used. In addition, triphosphates are less strongly hydrated than the diphosphate, which also tends to drive catalytic hydrolysis of the triphosphate to completion.

Clearly, the availability of a homogeneous population of protected mononucleotide triphosphates and enzymes capable of efficiently joining protected nucleotides to initiating substrates will enable the creation of a highly uniform population of synthetic polynucleotides resulting from stepwise phosphodiester bond formation.

SUMMARY OF THE INVENTION

A number of methods have been discovered by which the 3'-hydroxyl group of a deoxynucleotide triphosphate can be effectively protected and deprotected and wherein the protected nucleotide is utilized by a template independent polymerase to create a phosphodiester bond permitting the synthesis of oligonucleotides or polynucleotides having a desired predetermined sequence.

Therefore, in accordance with the present invention, a method is provided for the synthesis of a polynucleotide of a predetermined sequence of which method includes the steps of:

A. providing an initiating substrate comprising a nucleoside having an unprotected 3'-hydroxyl group; and B. reacting under enzymatic conditions in the presence of a catalytic amount of an enzyme the 3'-hydroxyl group of the initiating substrate with a nucleoside 5'-triphosphate having a removable blocking moiety protecting the 3' position of the nucleoside 5'-triphosphate and selected according to the order of the predetermined sequence, so that enzyme catalyzes the formation of a 5' to 3' phosphodiester linkage between the unprotected 3'-hydroxyl group of the initiating substrate and the 5'-phosphate of the nucleoside 5'-triphosphate to produce the polynucleotide.

In other embodiments of the present invention, the method further comprises the step:

C. removing the blocking moiety protecting the 3' position of said nucleotide 5'-triphosphate to produce an initiating substrate having an unprotected 3'-hydroxyl group.

In other embodiments, steps (b) and (c) are repeated at least once to add additional nucleotides to the initiating substrate by alternatively adding a nucleoside 5'-triphosphate with a removable blocking moiety at its 3' position, deblocking the 3' position of the terminal nucleoside and then adding another nucleoside 5'-triphosphate with a removable blocking group at its 3' position. Repetition of steps (b) and (c) can also be carried out to produce an oligonucleotide or polynucleotide having a predetermined sequence.

The present invention contemplates initiating substrates that are deoxynucleosides, nucleotides, single or double stranded oligonucleotides, single or double stranded polynucleotides, oligonucleotides attached to nonnucleoside molecules and the like.

The present invention contemplates embodiments in which the substrate is immobilized on a solid support. Preferred solid supports include cellulose, Sepharose, controlled-pore glass, silica, Fractosil, polystyrene, styrene divinyl benzene, agarose, and crosslinked agarose and the like.

The present invention contemplates the use of template independent polynucleotide polymerases such as terminal deoxynucleotidyl transferase from any number of sources including eukaryotes and protharyotes.

The methods of the present invention utilize removable blocking moieties that block the 3' position of nucleoside 5'-triphosphates used in the methods. Preferred removable blocking moieties can be removed in under 10 minutes to produce a hydroxyl group at the 3' position of the 3' nucleoside. Removable blocking groups contemplated include carbonitriles, phosphates, carbonates, carbamates, esters, ethers, borates, nitrates, sugars, phosphoramidates, phenylsulfenates, sulfates and sulfones.

The methods of the present invention contemplate removing the removable blocking moiety using a deblocking solution that preferably contains divalent cations such as Co++ and a biological buffer such as comprises a buffer selected from the group consisting of dimethylarsinic acid, tris[hydroxymethyl] amino methane, and 3-[m-morpholine] propanosulphonic acid. Other embodiments of the present invention utilize an enzyme present in the deblocking solution to remove the removable blocking moiety.

The present invention also contemplates methods in which the nucleoside 5'-triphosphate having the removable blocking moiety at its 3' position is immobilized in a solid support and reacted with free initiating substrates. The solid support is linked to the nucleoside 5'-triphosphate at the 3'-hydroxyl group, thereby acting as a removable blocking moiety at the 3' position. Attachment of the nucleoside to the support is transient, thereby enabling the release of the newly synthesized product from the support and regeneration of the free and unmodified 3'-hydroxyl to allow the next nucleotide addition to occur.

Thus, in some embodiments of the present invention the deblocking solution would remove the removable blocking moiety at the position of the nucleoside and thus release the growing polynucleotide from the solid support.

The present invention also includes polynucleotides having a predetermined sequence provided according to the methods of this invention. Applications for using polynucleotides and oligonucleotides of the present invention in molecular cloning and/or expression of genes, peptides or proteins.

Also contemplated by the present invention are compositions of matter comprising a catalytic amount of a template independent enzyme and a nucleoside 5'-triphosphate having a removable blocking moiety protecting the 3' position of said nucleoside 5'-triphosphate. Additional compositions of matter further comprising an initiating substrate are also contemplated.

BRIEF DESCRIPTION OF THE DRAWINGS

FIG. 1. A diagram showing enzymatic synthesis of an oligonucleotide using a template independent polymerase and a nucleoside 5' triphosphate having a removable blocking moiety at its 3' position is shown.

FIG. 2. A diagram of a nucleotide having a removable blocking moiety at its 3' position is shown.

FIG. 3. A diagram showing an apparatus for automating the enzymatic synthesis of polynucleotides is shown.

FIG. 4. A diagram showing an apparatus for automating the enzymatic synthesis of polynucleotides is shown.

BRIEF DESCRIPTION OF THE INVENTION

A. Definitions

DNA: Deoxyribonucleic acid.

RNA: Ribonucleic acid.

Nucleotide: A subunit of a nucleic acid comprising a phosphate group, a 5-carbon sugar and nitrogen containing base. In RNA, the 5-carbon sugar is ribose. In DNA, it is a 2-deoxyribose. The term also includes analogs of such subunits.

Nucleoside: Includes a nucleosidyl unit and is used interchangeably therewith, and refers to a subunit of a nucleic acid which comprises a 5-carbon sugar and a nitrogen containing base. The term includes not only those nucleosidyl units having A, G, C, T and U as their bases, but also analogs and modified forms of the naturally-occurring bases, such as pseudoisocytosine and pseudouracil and other modified bases (such as 8-substituted purines). In RNA, the 5-carbon sugar is ribose; in DNA, it is 2'-deoxyribose. The term nucleoside also includes other analogs of such subunits, including those which have modified sugars such as 2'-O-alkyl ribose.

Polynucleotide: A nucleotide multimer generally about 50 nucleotides or more in length. These are usually of biological origin or are obtained by enzymatic means.

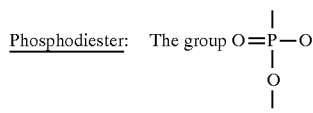

wherein phosphodiester groups may be used as internucleosidyl phosphorus group linkages (or links) to connect nucleosidyl units.

Hydrocarbyl: An organic radical composed of carbon and hydrogen which may be aliphatic (including alkyl, alkenyl, and alkynyl groups and groups which have a mixture of saturated and unsaturated bonds), alicyclic (carbocyclic), aryl (aromatic) or combination thereof; and may refer to straight-chained, branched-chain, or cyclic structures or to radicals having a combination thereof, as well as to radicals substituted with halogen atom(s) or heteroatoms, such as nitrogen, oxygen, and sulfur and their functional groups (such as amino, alkoxy, aryloxy, lactone groups and the like), which are commonly found in organic compounds and radicals.

Non-nucleoside monomeric unit: A monomeric unit wherein the base, the sugar and/or the phosphorus backbone or other internuclosidyl linkage of a nucleoside has been replaced by other chemical moieties.

Polypeptide and Peptide: A linear series of amino acid residues connected on to the other by peptide bonds between the alpha-amino and carboxyl groups of adjacent residues.

Protein: A linear series of greater than about 50 amino acid residues connected one to the other as in a polypeptide.

Gene: A segment of DNA coding for an RNA transcript that is itself a structural RNA, such as ribosomal RNA or codes for a polypeptide. The segment of DNA is also equipped with a suitable promoter, termination sequence and optionally other regulatory DNA sequences.

Structural Gene: A gene coding for a structural RNA and being equipped with a suitable promoter, termination sequence and optionally other regulatory DNA sequences.

Promoter: A recognition site on a DNA sequence or group of DNA sequences that provide an expression control element for a gene and to which RNA polymerase specifically binds and initiates RNA synthesis (transcription) of that gene.

Oligonucleotide: A chain of nucleosides which are linked by internucleoside linkages which is generally from about 2 to about 50 nucleosides in length. They may be chemically synthesized from nucleoside monomers or produced by enzymatic means. The term oligonucleotide refers to a chain of nucleosides which have internucleosidyl linkages linking the nucleoside monomer and, thus, includes oligonucleotide containing nucleoside analogs, oligonucleotide having internucleosidyl linkages such that one or more of the phosphorous group linkages between monomeric units has been replaced by a non-phosphorous linkage such as a formacetal linkage, a thioformacetal linkage, a sulfamate linkage, or a carbamate linkage. It also includes nucleoside/non-nucleoside polymers wherein both the sugar and the phosphorous moiety have been replaced or modified such as mopholino base analogs, or polyamide base analogs. It also includes nucleoside/non-nucleoside polymers wherein the vase, the sugar, and the phosphate backbone of a nucleoside are either replaced by a non-nucleoside moiety or wherein a non-nucleoside moiety is inserted into the nucleoside/non-nucleoside polymer. Thus an oligonucleotide may be partially or entirely phophonothioates, phosphorothioate phosphorodithioate phosphoramidate or neutral phosphate ester such as phosphotriesters oligonucleotide analogs.

Removable Blocking Moiety: A removable blocking moiety is a moiety which is attached to the oxygen at the 3' position of a nucleoside or the equivalent position in a nucleoside analog. The removable blocking moiety prevents reaction of the 3' oxygen when present and is removable under deblocking conditions so that the 3' oxygen can then participate in a chemical reaction.

A. Methods

Generally, the present invention provides methods for synthesizing oligonucleotides and polynucleotides having a predetermined sequence using a template independent polymerase and nucleoside having the 3' position blocked with a removable blocking moiety so that single nucleosides are added to the growing oligonucleotide. Single nucleosides are added to the growing chain by removing the blocking moiety at the 3' position of the terminal nucleoside of the growing oligonucleotide so that the next blocked nucleoside can be added to the oligonucleotide. This process is then repeated until the oligonucleotide having the predetermined sequence is produced.

Thus, in accordance with this embodiment of the present invention, a method comprises the steps of:

(a) providing an initiating substrate comprising a nucleoside having an unprotected 3'-hydroxyl group; and (b) reacting under enzymatic conditions in the presence of a catalytic amount of an enzyme said 3'-hydroxyl group of said initiating substrate with a nucleoside 5'-triphosphate having a removable blocking moiety protecting the 3' position of said nucleoside 5'- triphosphate and selected according to the order of said predetermined sequence, whereby said enzyme catalyzes the formation of a 5' to 3' phophodiester linkage between said unprotected 3'-hydroxyl group of said initiating substrate and the 5'-phosphate of said nucleoside 5'-triphosphate to produce said polynucleotide.

In preferred embodiments, the methods of the present invention further comprises the step of:

(c) removing the blocking moiety protecting the 3' position of said nucleoside 5'-triphosphate to produce an initiating substrate having an unprotected 3'-hydroxyl group.

This additional step regenerates a reactive atom at the 3' position of the terminal nucleoside so that this atom can be used to form a bond with the next nucleoside and thus extend the length of the oligonucleotide by one nucleoside.

The methods of the present invention also include methods in which the above steps (b) and (c) are repeated at least once to produce an oligonucleotide. This process can be repeated many times to produce oligonucleotides of selected length. This process can also be repeated many times such that each particular nucleoside added to the oligonucleotide having a preselected sequence.

1. Initiating Substrates

An initiating substrate of the present invention is prepared containing a nucleoside with a free and unmodified 3'-hydroxyl group. As is well understood by those of ordinary skill in the art, nucleotide derivatives of the nucleosides adenosine, cytidine, guanosine, uridine and thymidine can be assembled to form oligonucleotides and polynucleotides.

According to the method of the present invention, the initiating substrate may contain a single nucleoside having a free and unmodified 3'-hydroxyl group, or a preassembled oligo- or polynucleotide may be provided as an initiating substrate, so long as the oligo- or polynucleotide has a free and unmodified 3' -hydroxyl group.

One skilled in the art will understand that an initiating substrate could be provided in a form in which a nucleoside has a removable blocking moiety at its 3' position which is subsequently removed using a deblocking process so that the initiating substrate now has the free unprotected 3' hydroxyl group useful in the present invention.

The initiating substrates of the present invention include the termini of polynucleotides frequently generated and used in various cloning and molecular biology techniques. Examples of these initiating substrates include the termini of DNA or RNA vectors, single-stranded or double-stranded fragments, single-stranded or double-stranded RNA fragments and RNA or DNA oligonucleotides.

In the preferred embodiments, initiating substrates will consist wholly or in part of an oligo- or polynucleotide. The initiating substrate can be any arrangement of nucleosides which enables the enzyme to create a phosphodiester bond between the 3'-hydroxyl of a nucleoside and the 5'-phosphate of a mononucleotide. Initiating substrates may be based wholly or in part on ribonucleic acids (RNA) or deoxyribonucleic acids (DNA) and may be single stranded or multi-stranded. In addition, initiating substrates can include other types of naturally occurring or synthetic molecules (non-nucleosides) which may enable or enhance the ability of the enzyme to create a phosphodiester bond or which may facilitate the manipulation of reaction components and by-products. An example of this would be a linker molecule (commonly used linkers consist of C, O, N, and H e.g. AFFI-GEL™ 10: R—OCH$_2$CONH(CH$_2$)$_2$NHCO (CH$_2$)$_2$COON(CH$_2$)$_2$ which would serve to provide a convenient method for attaching an initiating substrate to a solid support.

The sequential creation of phosphodiester bonds and hence the addition of nucleotides to the initiating substrate may be performed entirely in solution, or the initiating substrate may be attached to an insoluble matrix. Attachment to an insoluble matrix will permit the rapid separation of the substrate from unreacted reagents in order to prepare the substrate for the addition of the next nucleotide. For this reason, the substrate is preferably affixed to a solid support matrix during each reaction creating a phosphodiester bond.

Insoluble matrices suitable for use as solid supports include cellulose, SEPHAROSE™, controlled-pore glass (CPG), polystyrene, silica, agarose, and the like.

Reagents, buffers and solvents suitable for use with the present invention are capable of flowing through the solid support matrix, by which means the initiating substrate is brought into contact with these materials. The growing nucleotide chain remains attached to the solid support as the various reagents, buffers and solvents sequentially flow therethrough. The solid support matrix is preferably contained within a synthesis column, to which reagents, buffers and solvents are provided.

Attachment of the initiating substrate to the solid support can be by covalent bonding. Numerous methods for the covalent attachment of molecules to insoluble matrices have been described and are well understood by those of ordinary skill in the art. In the preferred embodiment an oligonucleotide chain may be linked to alkylamine derivatized polystyrene or CPG by way of a covalent phosphoramidate bond although numerous strategies for linking oligonucleotides to solid supports have been described. The choice of an appropriate linking strategy will depend on the specific requirements of stability, charge interactions, solubility and the like.

Alternatively, attachment of the initiating substrate to the solid support can be by non-covalent interactions. Numerous methods for the transient attachment of molecules to insoluble matrices have been described and are well understood by those of ordinary skill in the art. For example, an oligonucleotide derivative containing single or multiple biotin molecules may be attached to avidin-agarose or streptavidin-agarose to form a non-covalent linkage between the oligonucleotide and the insoluble agarose matrix.

In general, it is envisioned that single and double stranded oligo- and polynucleotides based on DNA or RNA may be covalently or non-covalently bound to solid supports to form a variety of initiating substrates. Regardless of the strategy employed to attach an initiating substrate to an insoluble matrix, a nucleoside with a free and unmodified 3'-hydroxyl group will always be available for enzyme catalyzed creation of a phosphodiester bond.

2. Template Independent Enzymes

Mononucleotides are added to the free and unmodified 3'-hydroxyl group of the initiating substrate by reacting the substrate with the 5'-phosphate of the selected mononucleotide in the presence of a catalytic amount of an enzyme capable of creating the phosphodiester bond covalently linking the 5'-phosphate of the mononucleotide with the 3'-hydroxyl of the substrate. The enzyme is preferable a template independent enzyme such as a template independent polynucleotide polymerase. Template independent enzymes such as template independent polynucleotide polymerases are capable of catalyzing the formation of a phosphodiester bond between the nucleotides without requiring the presence of a complementary nucleotide strand for activity. Thus, the template independent enzymes such as template independent polynucleotide polymerases are able to catalyze the formation of single-stranded nucleic acid polymers without requiring a complementary nucleic acid strand to act as a template. Examples of template independent polynucleotide polymerases include terminal deoxynucleotidyl transferases. Template independent polynucleotide polymerases can be isolated from a number of sources including calf thymus and other sources of lymphocytes. A particularly preferred polymerase is terminal deoxynucleotidyl transferase (TdTase, EC 2.7.7.31).

Enzymes capable of being utilized with the present invention can be readily identified by those of ordinary skill in the art, and are employed under appropriate and well understood conditions. Example enzymatic conditions for deoxynucleotidyl transferase include a pH of 6.8 maintained by a potassium cacodylate buffer, 8 mmol/l of $MgCl_2$, 1 mmol of β mercaptoethambol, 0.33 mmol/l of $ZnSO_4$. One skilled in the art will understand that these enzymatic conditions may vary while still allowing the enzyme to catalyze the desired reaction.

3. Nucleosides Having Removable Blocking Moieties

In accordance with the present invention, the mononucleotide has its 3' position protected by a removable blocking moiety so that a single phosphodiester linkage is formed between the free 3'-hydroxyl of the initiating substrate and the 5'-phosphate group of the mononucleotide. The removable blocking moiety protecting the 3' position of the mononucleotide prevents the catalytic creation of multiple phosphodiester bonds and hence multiple nucleotide additions.

The present invention contemplates a nucleoside 5'-phosphate of the present invention has a removable blocking moiety protecting the 3' position having the following formula:

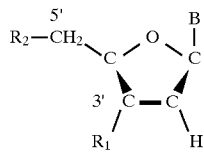

wherein R2 is triphosphate, diphosphate or monophosphate; and wherein R1 is a hydrocarbyl. In preferred embodiments the nucleoside 5' phosphate of the above formula has an R2 group which is triphosphate and an R1 group which is a hydrocarbyl.

Nucleotides having a removable blocking moiety protecting the 3' position suitable for use with the present invention have a structure corresponding to Formula 1, that has a structure which is compatible with the utilization of the entire nucleotide for the creation of a phosphodiester bond by the enzyme.

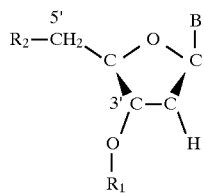

FORMULA 1

B is the nucleotide base and $R_2$ represents the appropriate mono-, di- or triphosphate. $R_1$ can be an ester linkage, $COR_1'$, which forms the structure nucleotide-3'-O—CO—$R_1'$. $R_1'$ can be any alkyl or aryl group compatible with the utilization of the molecule by the enzyme for the creation of an internucleotide phosphodiester bond. The chemistry of esters as protecting groups for hydroxyls is well established. Removable blocking moieties including formate, benzoyl formate, acetate, substituted acetate, propionate, isobutyrate, levulinate, crotonate, benzoate, napthoate and many other esters have been described in detail (See, Greene, T. W., *Protective Groups in Organic Chemistry*, John Wiley & Sons, New York, 1981). Esters in general are readily removed, usually in the presence of base, to regenerate the hydroxyl group and thus are useful as removable blocking moieties.

Ester removable blocking moieties are formed by reacting the nucleotide with the appropriate acid anhydride. Alternatively, a carboxylic acid can be esterified with the 3'-hydroxyl of the nucleotide in the presence of water after activation by reaction with carbonyl diimidazole (See, Schafer et al., *Meth Enzymol.*, 126, 682–712.)

The present invention also contemplates a nucleoside 5'-phosphate having a removable blocking moiety protecting the 3' position which is an ester and which has the following formula:

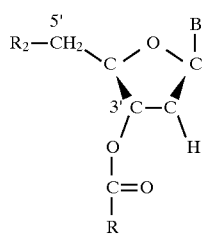

wherein R2 is triphosphate, diphosphate or monophosphate; and wherein R1 is any aliphatic or aromatic organic ester.

The present invention also contemplates a nucleoside 5'-phosphate having a removable blocking moiety protecting the 3' position which is an ester and which has the following formula:

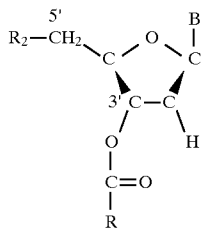

wherein R is selected from the group consisting of: formate, benzoylformate, chloroacetate, dicholoroacetate, trichloroacetate, trifluoroacetate, methoxyacetate, triphenylmethoxyacetate, phenoxyacetate, p-chlorophenoxyacetate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, phenylacetate, 3-phenylpropionate, 3-benzoylpropionate, isobutyrate, monosuccinoate, 4-oxopentanoate, pivaloate, adamanioate, crotonate, 4-methoxycrotonate, (E)-2-methyl-2-butenoate, o-(dibromomethyl)benzoate, o-(methoxycarbonyl)benzoate, p-phenylbenzoate, 2,4,6-trimethylbenzoate and α-naphthoate.

The present invention also contemplates a nucleoside 5'-phosphate having a removable blocking moiety protecting the 3' position which is an ester and which has the following formula:

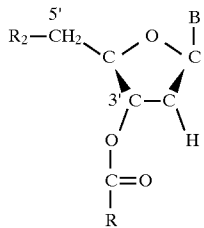

wherein R2 is triphosphate, diphosphate or monophosphate; and wherein R is selected from the group consisting of: H, $CH_3$, $CH_3(CH_2)_N$ where N is an integer from 1 to 12, $(CH_3)_{x+1}(CH)_x$ where x is an integer from 1 to 12, $(CH_3)_{x+1}(CH)_x(CH_2)_n$ where x and n are independent integers from 1 to 12, $C_x(CH_3)_{3x-(x-1)}(CH2)_n$ where x and n are independent integers from 1 to 12,

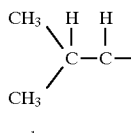

and

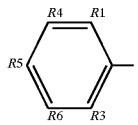

where R1, R3, R4, R5 and R6 is $CH_3$, H or $NO_2$.

In preferred embodiments, the nucleoside 5' phosphates of the present invention are deoxynucleoside 5' triphosphate having a removable blocking moiety protecting the 3' position which can be any of the blocking groups disclosed in this specification or equivalents of those groups.

An alternative type of removable blocking moiety utilizes an ether linkage which forms the structure nucleotide —3'—O—R'$_1$. In this instance R'$_1$ can be methyl, substituted meythyl, ethyl, substituted ethyl, butyl, allyl, cinnamyl, benzyl, substituted benzyl, anthryl or silyl. The chemistry involved in using ethers as removable blocking moieties for hydroxyls is well known in the art. Numerous ethers have been described and are useful for transiently protecting hydroxyls and similar chemical groups.

In other embodiments, a nucleoside 5' phosphate of the present invention has a removable blocking moiety protecting the 3' position which is an ether and which has the following formula:

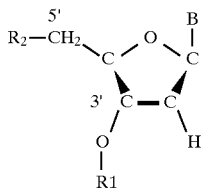

wherein R2 is triphosphate, diphosphate or monophosphate; and wherein R1 is an ether selected from the group consisting of a substituted or unsubstituted: aliphatic group, aromatic group or silyl group.

In other embodiments, a nucleoside 5' phosphate of the present invention has a removable blocking moiety protecting the 3' position which is an ether and which has the following formula:

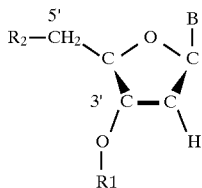

wherein R2 is triphosphate, diphosphate or monophosphate; and wherein R1 is an ether selected from the group consisting of a methyl, methoxymethyl, methylthiomethyl, benzyloxymethyl, t-butoxymethyl, 2-methoxyethoxymethyl, 2,2,2-trichloroethoxymethyl, bis(2-chloroethoxy)methyl, 2-(trimethylsilyl)ethoxymethyl, tetrahydropyarnyl, 3-bromotetrahydropyranyl, tetrahydrothiopyranyl, 4-methoxytetrahydropranyl, 4-methoxytetrahydrothiopyranyl, 4-methoxytetrahydrothiopyranyl S,S-dioxido, tetrahydrofuranyl, tetrahydrothiofuranyl, 1-ethoxyethyl, 1-methyl-1-methoxyethyl, 1-(isopropoxy)ethyl, 2,2,2-trichloroethyl, 2-(phenylselenyl)ethyl, butyl, allyl, cinnamyl, p-chlorophenyl, benzyl, p-methoxybenzyl, o-nitrobenzyl, p-nitrobenzyl, p-halobenzyl, p-cyanobenzyl, 3-methyl-2-picolyl N-oxido, diphenylmethyl, 5-dibenzosuberyl, triphenylmethyl, α-naphthyldiphenylmethyl, p-methoxyphenyldiphenylmethyl, p-(p'-bromophenacyloxy)phenyldiphenylmethyl, 9-anthryl, 9-(9-phenyl-10-oxo)anthryl, benzisothiazolyl S,S-dioxido, trimethylsilyl, triethylsilyl, isopropyldimethylsilyl, t-butyldimethylsilyl, (triphenylmethyl)dimethylsilyl, methyldiisopropylsilyl, methyldi-t-butylsilyl, tribenzylsilyl, tri-p-xylylsilyl, triisopropylsilyl and triphenylsilyl.

In preferred embodiments, a nucleoside 5' phosphate of the present invention has a removable blocking moiety protecting the 3' position which is an ether and which has the following formula:

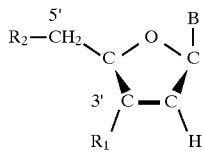

wherein R2 is triphosphate, diphosphate or monophosphate; and wherein R1 is selected from the group consisting of bis(2-chloroethoxy)methyl ether, 4-methoxytetrahydropyranyl ether, tetrahydrofuranyl ether, 1-ethoxyethyl ether, tri(p-methoxyphenyl)methyl ether, di(p-methoxy)phenylmethyl ether, t-butyldimethylsily ether.

In more preferred embodiments, a nucleoside 5'phosphate of the present invention has a removable blocking moiety protecting the 3' position which is an ether and which has the following formula:

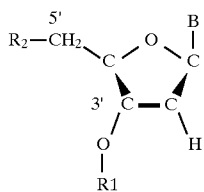

wherein R2 is triphosphate, diphosphate or monophosphate; and wherein R1 is $CH_3$, $CH_3(CH_2)_N$ where N is an integer from 1–10, methyl, methoxymethyl, methoxyethoxymethyl, trimethlsilyl, and triethylsilyl. In a more preferred embodiment, the nucleoside 5'-phosphate of the present invention has an R1 group which is $CH(OC_2H_5)CH_3$ and R2 is triphosphate and said nucleoside 5'-phosphate is a deoxynucleoside.

Additional well known removable blocking moieties useful for protecting for hydroxyls include carbonitriles, phosphates, carbonates, carbamates, borates, nitrates, phosphoramidates, and phenylsulfenates. Most of these chemical modifications to the nucleotide can be removed by chemical reactions. Some modifications may also be removed by enzymatic digestion resulting in the regeneration of the 3' hydroxyl. These would include phosphates, glycosides, and certain esters.

In other embodiments, a nucleoside 5'-phosphate of the present invention has a removable blocking moiety protecting the 3' position having the following formula:

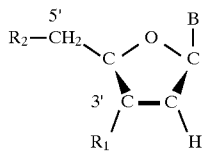

wherein R2 is triphosphate, diphosphate or monophosphate; and wherein R1 is selected from the group consisting of phosphate, phosphoramidate and phosphoramide. In preferred embodiments the nucleoside 5' phosphate of the above formula has an R2 group which is triphosphate and an R1 group which is phosphate.

More preferred embodiments of the present invention contemplate a nucleoside 5'-phosphate having a removable blocking moiety protecting the 3' position which has the following formula:

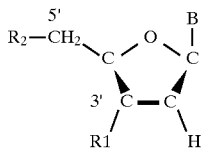

wherein R2 is triphosphate, diphosphate or monophosphate; and wherein R1 is selected from the group consisting of phosphate, toluic acid ester or ethoxyethyl ether.

The present invention also contemplates a nucleoside 5'-triphosphate having a removable blocking moiety protecting the 3' position which is an ester produced by directly esterifying the nucleoside 5'-triphosphate. In preferred embodiments the nucleoside 5'-triphosphate has an ester is benzoate or acetate as the removable blocking moiety protecting the 3' position. In the more preferred embodiments, the nucleoside 5'-triphosphate produced by direct esterification is a deoxynucleoside.

The present invention also contemplates a nucleoside 5'-triphosphate having a removable blocking moiety protecting the 3' position which is an ether produced by directly attaching an ether to the nucleoside 5'-triphosphate.

Particularly preferred are deoxynucleoside 5'triphosphates produced by directly attaching an ether to the 3' position.

Attachment of the nucleotide having a removable blocking moiety protecting the 3'- position to the free and unmodified 3'-hydroxyl of the initiating substrate is then accomplished by reacting [incubating] the aforementioned nucleotide and the substrate with an enzyme capable of forming a phosphodiester bond between the two. Specifically, this bond would link the 5'-phosphate of the mononucleotide with the 3'-hydroxyl of the initiating substrate. This reaction can be performed either free in solution or, in one embodiment of the invention, the initiating substrate is immobilized on a solid support.

Particularly preferred are removable blocking moieties and deblocking reaction conditions that allow the blocking moiety to be removed in under 10 minutes to produce a hydroxyl group at the 3' position of the 3'-terminal nucleoside. Other preferred removable blocking moieties and deblocking conditions allow the blocking moiety to be removed in less than 8, 7, 6, 5, 4, 3, 2, or 1 minutes, 4. Reactions In preferred embodiments, the preferred enzyme is TdTase, and specific examples of uses of this enzyme are set forth below. However, the present invention should not be considered limited to the TdTase catalyzed synthesis of DNA and use of other enzymes capable of catalyzing the formation of a 5' to 3' phosphodiester linkage between the 3' hydroxyl group of the substrate and the 5' phosphate of the nucleoside having the removable blocking moiety is contemplated by the present invention. One skilled in the art will understand that enzyme reaction conditions are selected to allow the desired catalysis to occur and may be performed under appropriate conditions, and these conditions are well known in the art.

The reacting is performed typically between 25° C. and 42° C. for an appropriate period of time, typically between about one minute and about 30 minutes. Very short reaction times may be particularly useful if the removable blocking moiety is unstable.

For TdTase catalyzed reactions, the enzymatic conditions, which may serve as the solution in which the substrate is reacted, contains from about 0.20 and about 200 $\mu$M of the nucleotide having the removable blocking moiety protecting the 3'-hydroxyl, and from about 0.20 to 200 µM of free and unmodified 3'-hydroxyls derived from the initiating substrate. One particularly preferred buffer contains from about 10 to about 500 mM potassium cacodylate buffer (pH between 6.5 and 7.5), and from about 0.01 to about 10 mM of a divalent cation (e.g. $CoCl_2$ or $MnCl_2$). Other buffer compositions and components may be suitable for particular desired embodiment of the present invention.

For example, enzymatic conditions for deoxynucleotidyl transferase include a pH of 6.8 maintained by a potassium cacodylate buffer, 8 mmol/l of $MgCl_2$, 1 mmol.l of β mercaptoethanol, 0.33 mmol/l of $ZnSO_4$. One skilled in the art will understand that these enzymatic conditions may vary while still allowing the enzyme to catalyze the desired reaction.

The enzyme capable of catalyzing the formation of 5' to 3' phosphodiester linkages between the 3' hydroxyl group of the initiating substrate and the 5' phosphate of the nucleoside being added is present in a catalytic amount. A catalytic amount of enzyme is typically sufficient to catalyze the formation of phosphodiester bond between greater than 99% of the free 3' hydroxyls of the initiating substrate and the 5' phosphate of the nucleoside within 1 hour. Preferably, the catalytic amount of enzyme and the enzymatic conditions are such that greater than 99% of the free 3' hydroxyls of the initiating substrate are reacted within 10 minutes. In other preferred embodiments, the catalytic amount of enzyme and the enzymatic conditions are such that greater than 90% of the free 3' hydroxyls of the initiating substrate are reacted in less than 5 minutes, for example 4, 3, 2 or 1 minutes. In other preferred embodiments, the catalytic amount of enzyme and enzymatic conditions are such that greater than 99% of the free 3' hydroxyls of the initiating substrate are reacted within 2 minutes.

The TdTase enzyme is present in the buffer at a level between about 1 and 200 units per µL. One unit of TdTase catalyzes the transfer of 1 nmol of dATP to $p(dT)_{6-12}$ in 60 minutes at 37° C. Commercially available forms of TdTase include calf thymus TdTase, available from a variety of suppliers (e.g. Sigma Chemical Co., St. Louis Mo., Promega Corp, Madison, Wis., Gibco-BRL, Gaithersburg, Md.). Calf thymus TdTase may also be prepared by the procedures described by Modak, *Biochemistry*, 17, 3116–20 (1978), and by Bollum, *Fed. Proc. Soc. Exp. Biol. Med.* 17, 193 (1958).

While the substrate containing a free and unmodified 3'-hydroxyl group and the mononucleotide having the removable blocking moiety protecting the 3'-hydroxyl group can be reacted in the presence of the TdTase in the buffer solution, the substrate is preferably immobilized on a solid support, and more preferably in a synthesis column to which the buffer solution containing the reaction components is delivered.

After the appropriate incubation time, the enzyme, unreacted mononucleotide, buffer and divalent cation are separated from the initiating substrate. If the reaction was performed using a free and soluble substrate, it can be separated by conventional size exclusion chromatography or similar types of separation techniques including but not limited to ion exchange chromatography and affinity chromatography. For initiating substrates immobilized on solid supports, separation is achieved by washing the support with water or a suitable buffer.

One advantage to the present invention is that the level of unreacted hydroxyl groups on the initiating substrate after the aforementioned enzyme reaction can be exceptionally low, less than 0.1%. This minimizes the necessity for capping unreacted hydroxyl groups. In some embodiments of the present invention it may be desirable to cap the unreacted substrates before the next step in the synthesis cycle. The appropriate chemistry for accomplishing this can be derived from any of the protection strategies described previously but must be permanently affixed during all the subsequent cycles. An example of capping is acetylation by reaction of free 3'-hydroxyls with acetic anhydride and pyridine which would be applicable when acetylation (or other esterifications) are not used as the protecting group on the mononucleotide. Alternatively capping can be accomplished by reaction with t-butyldimethylchlorosilane in acetonitrile and pyridine to form a silyl ether which would be applicable when similar ethers are not used to protect the mononucleotide. In the preferred embodiment, these reactions are intended primarily for modifying immobilized initiating substrates in order to rapidly and efficiently provide appropriate capping conditions.

After the appropriate incubation time, capping reagents are separated from the initiating substrate. If the reaction was performed using a soluble substrate, it can be separated by conventional size exclusion chromatography or similar types of separation techniques including but not limited to ion exchange and affinity chromatography. For initiating substrates immobilized on solid supports, separation is achieved by washing the support with water or a suitable buffer.

The removable blocking moieties protecting the 3' position on the initiating substrate after the reaction may be removed or deblocked (deprotected) to regenerate a free and unmodified 3'-hydroxyl available for addition of the next nucleotide. One skilled in the art will understand that this may be accomplished by either chemical or enzymatic methods. For example, ester protecting groups may be removed using an esterase when $R_1$ of the ester protecting group discussed above is a suitable substrate for the esterase. Otherwise, the ester linkage may be cleaved by base hydrolysis, which is accomplished by contacting the protected 3'-hydroxyl group with a suitable concentration of base for a sufficient period of time. Cleavage of ester protecting groups has been well studied and appropriate reaction conditions can be readily identified that will cleave the ester but will not cleave the linkage used for capping (e.g. an ether).

The present invention incorporates the unexpected discovery that certain removable blocking moieties, the aromatic 3'-O esters of deoxynucleotide triphosphates, are unstable in commonly used buffers containing divalent cations. The instability is attributable to the presence of both the buffer and the divalent cation, and does not result from the presence of the buffer alone or the cation alone. Buffers destabilizing the ester protecting groups may contain dimethylarsinic acid (cacodylic acid), tris(hydroxymethyl) aminomethane, sodium acetate and sodium phosphate. Divalent cations destabilizing to ester blocking groups include cobalt, manganese and magnesium ions. The toluic acid ester of a deoxynucleotide triphosphate is unstable in a mixture of 1 mM $CoCl_2$, 100 µM potassium cacodylate, pH 6.8.

Conditions for the removal of removable blocking moieties such as ethers, carbonates, nitrates, and other protecting groups are well studied and many are compatible with the integrity of a polynucleotide chain. Removal of blocking moieties such as phosphate protecting groups, the hydroxyl is regenerated by enzymatic digestion with a phosphatase. For removal of blocking moieties when the protecting group is a sugar moiety, regeneration of the hydroxyl can be accomplished by enzymatic hydrolysis using a glycosidase.

If the removal or deblocking reaction is performed in solution, the deprotection reagents are simply added to the solution. If the reaction is performed with the initiating substrate immobilized on a solid support, then the hydroxyl group regeneration step is performed by washing the solid support with the deprotection reagents. When synthesis columns are utilized to contain the solid support, the hydroxyl group regeneration step is performed by washing the column with the appropriate agents.

After the appropriate period for removal, the initiating substrate (including both those that received an additional nucleotide and those that are capped) is again separated from the other reaction components. If the reaction was performed using a soluble substrate, it can be separated by conventional size exclusion chromatography or similar types of separation techniques including but not limited to ion exchange and affinity chromatography. For initiating substrates immobilized on solid supports, separation is achieved by washing the support with water or a suitable buffer.

As will be appreciated, the above described steps of enzyme catalyzed phosphodiester bond formation between a nucleotide having a removable blocking moiety at its 3' position and an initiating substrate, separation of the initiating substrate from reaction components, capping of unreacted initiating substrate, again separating the initiating substrate from reaction components, removing the removable blocking moiety to regenerate the 3'-hydroxyl group, and again separating the initiating substrate from reaction components are repeated as necessary until the desired object polynucleotide chain is completely synthesized.

Cleavage of a newly synthesized polynucleotide strand from the solid support and/or from the initiating substrate can be accomplished by either chemical or enzymatic reactions. In the case of a chemical reaction, if the initiating substrate terminal nucleoside (containing the free and unmodified 3'-hydroxyl group) is a deoxyguanosine methylated at the 7 position of the base:

Support-dCCCCCCCCCCC-Me$^7$-G-object polynucleotide (SEQ. ID No. 1) reaction with 1M piperidine in water at 90° C. will cleave the chain at this position yielding only the desired polynucleotide in solution. This method can yield a polynucleotide chain containing only the predetermined sequence and can be performed either on immobilized chains (to effect cleavage) or on solution synthesized chains to remove the initiating substrate. Alternatively, the dG$^{7me}$ can be positioned at any location within the initiating substrate or the object polynucleotide where cleavage is desired. Other examples of modified base-specific cleavage of polynucleotide chains have been extensively described in the literature (See, Ambrose and Pless, *Meth. Enzymol.,I Vol* 152: 522–538.)

Enzymatic removal of the polynucleotide chain may be accomplished by reaction with a specific restriction endonuclease. For example, if the initiating substrate oligonucleotide has the following structure:

Support-dCCCCCCCCCCCCCCCTGCA-3'-OH (SEQ ID No. 2) and the object polynucleotide begins with a G, the resulting newly synthesized chain can be cleaved from the support by reaction with Pst 1 restriction enzyme. This method assumes there are no additional Pst 1 restriction sites in the newly synthesized chain and that one has annealed an appropriate oligonucleotide to the Pst 1 site to render it in a double stranded form for recognition by the enzyme (e.g. an annealing oligonucleotide with the following structure: 3'-dGGGGGGGGGGGGGGGACGTC-5' (SEQ ID No. 3) for the example above). Depending on the desired first nucleotide of the object polynucleotide, as well as the ultimate sequence of the polynucleotide, one can choose from a wide variety of restriction enzymes to accomplish the cleavage of only the desired sequence. This method can yield a polynucleotide chain containing only the predetermined sequence and can be performed either on immobilized chains (to effect cleavage) or on solution synthesized chains to remove the initiating substrate. Alternatively, appropriate restriction endonuclease recognition sequences can be positioned at any location within the initiating substrate or the object polynucleotide where cleavage is desired.

The combined initiating substrate and object polynucleotide can be cleaved from the solid support by chemical methods. How the cleavage is performed will depend upon the nature of the initiating substrate and how it was attached to the solid support. Covalent labile bonds, such as for example a trityl group, can be cleaved by washing the support with an appropriate protic acid. Numerous other cleavage strategies have been described. In the case of a non-covalent attachment, as for example avidin-biotin binding, release of the combined substrate and object polynucleotide will occur upon incubation with 8M guanidine-HCl, pH 1.5.

If the entire synthesis was performed using a soluble initiating substrate, the initiating substrate containing the object polynucleotide can be separated from the various capped oligo- and polynucleotides by conventional chromatographic techniques, such as polyacrylamide gel electrophoresis. Similarly, if the initiating substrate is cleaved from the object polynucleotide by chemical or enzymatic means (e.g. by reaction with piperidine or by restriction endonucleases digestion as described above) conventional chromatography can be used to purify the object polynucleotide.

If the synthesis was performed using an initiating substrate immobilized to a solid support, cleavage from the solid support can be accomplished by either chemical or enzymatic means to retrieve either the combined initiating substrate and object polynucleotide or the object polynucleotide alone. In each instance, the object polynucleotide will be contaminated with capped oligo- and polynucleotides which can be separated from the object polynucleotide by polyacrylamide gel electrophoresis.

An alternative strategy for the synthesis and recovery of the object polynucleotide involves immobilization of the nucleotide. In this instance, the nucleotide is protected at the 3'-hydroxyl by a linker which is attached to a solid support. The linker attachment to the nucleotide can be by an ester or by any of the aforementioned protecting group strategies. Solid supports containing various functional groups (e.g. amines, amides, biotin, avidin, and the like) are generally available and can be adapted to the particular requirements of the nucleotide linker. For example, a nucleotide linker containing a biotin molecule can be bound to agarose using an avidin functional group attached to the agarose.

Using an immobilized nucleotide, the TdTase reaction would join a free initiating substrate, in solution, to the immobilized nucleotide, thereby immobilizing only those initiating substrates which have participated in the enzyme reaction. Initiating substrates which had not participated in the TdTase reaction would be easily removed by rinsing the solid support with an appropriate buffer. Regeneration of the 3' hydroxyl on the initiating substrate is accomplished by the same techniques as described previously.

Subsequent to the regeneration and cleavage step, the initiating substrate is rinsed away from the solid support and separated from the regeneration/cleavage solution containing free nucleotides by conventional techniques such as size exclusion chromatography, ion exchange or affinity chromatography. The next immobilized nucleotide, contained on a new population of solid support particles, is then mixed with the initiating substrate and the appropriate buffers in order to repeat the TdTase coupling reaction.

By immobilizing the nucleotide rather than the initiating substrate, a capping reaction is obviated since the object polynucleotide is separated from unreacted initiating substrate at every cycle. Similarly, if the cleavage reaction fails to release all of the object polynucleotide chains, those polynucleotides which continue to be attached to the solid support are removed prior to the subsequent TdTase reaction.

It is envisioned that various newly synthesized polynucleotide chains will subsequently be joined together by a polymerase/ligase type of reaction in order to form longer polynucleotide sequences that are in a double stranded form. For example, newly synthesized polynucleotides A and B may have the structures depicted below:

A: 3'-p(dN)-dCCCCCCCCC-5' (SEQ ID No. 4)

B: 3'-p(dN)-dGGGGGGGGG-5' (SEQ ID No. 5)

where p(dN) is the predetermined object polynucleotide sequence unique to either the A or B polynucleotide. In the presence of the Klenow fragment of DNA polymerase I, and T4 DNA ligase, as well as the appropriate buffers and nucleotides, a double stranded polynucleotide will be formed in which the two object polynucleotides have been "stitched" together to form the longer double stranded polynucleotide C:

C: 5'-p(dN)-dCCCCCCCCCp(dN)-3' (SEQ ID No. 4)

3'-p(dN)-dGGGGGGGGGp(dN)-5' (SEQ ID No. 5)

This reaction can be performed when one of the polynucleotides is still attached to a solid support or when both polynucleotides have been released into solution by the techniques described previously.

B. Polynucleotides

The present invention contemplates oligonucleotides and polynucleotides produced using the methods of this invention. These polynucleotides preferably have a predetermined nucleotide sequence that was produced by selecting the order in which the individual nucleotides were added to the initiating substrate so when synthesis is completed a polynucleotide having a preselected sequence is produced. Alternatively, random combination of polynucleotides could also be produced by introducing all four blocked nucleotides during an individual coupling reaction or during numerous individual coupling reactions.

In preferred embodiments, a polynucleotide produced according to the methods of this invention is greater than five nucleotides in length. Polynucleotides produced according to the methods of the present invention may contain large numbers of nucleotides, for example 10, 20, 30, 40, 50, 60, 70, 80, 90, 100, 110, 120, 130, 140, 150, 160, 170, 180, 190, 200 and greater than 200 nucleotides. The length of a polynucleotide produced using the methods of the present invention may be of a length that is intermediate between the aforementioned nucleotide lengths, such as 5, 15, 16, 25, 26 or any other numeral intermediate between the specific lengths. The length of the polynucleotide produced according to the present invention is limited only by the efficiency of the processes of the present invention.

Polynucleotides produced by the methods of the present invention can contain nucleotide sequences that have a variety of biologic and molecular biologic uses. One skilled in the art will understand the uses for long polynucleotides having a predetermined sequence. For example, many manipulations commonly performed in modern molecular biology could be greatly simplified through the availability of inexpensive, long polynucleotides having a predetermined sequence.

Examples of molecular biology procedures and manipulations that would be simplified using the polynucleotides produced according to the methods of the present invention include cloning and expression of various nucleic acids both in vitro and in vivo. For examples of techniques and manipulations that are simplified using polynucleotides produced using the methods of the present invention see, *Methods in Enzymology,* Vol. 152 edited by Berger and Kimmel; Maniatis et al., *Molecular Cloning a Laboratory Manual,* Cold Spring Harbor Press, 1990; *Current Protocols in Molecular Biology,* edited by Ausubel et al., John Haley and Sons, New York, 1987.

For example, polynucleotides of the present invention could be used to introduce restriction sites into a nucleic acid, to introduce various nucleotide sequences having biological activity such as promoters, and to adjust reading frames. The number of possible applications using oligonucleotide and polynucleotide produced according to the present invention is large as one skilled in the art will understand. Oligonucleotides and polynucleotides produced according to the present invention are especially useful when the application requires long oligonucleotides and polynucleotides.

C. Compositions of Matter

The present invention also contemplates compositions of matter comprising a catalytic amount of a template independent enzyme and a nucleoside 5'-triphosphate having a removable blocking moiety protecting the 3' position of the nucleoside 5' triphosphate and other preferred compositions further comprise an initiating substrate of the present invention.

The present invention contemplates compositions having an amount of template independent enzyme capable of catalyzing the formation of a 5' to 3' phosphodiester linkage between 99 percent of the unprotected 3' hydroxyl groups present on an initiating substrate of the present invention and a nucleoside 5'-triphosphate having a removable blocking group protecting its 3' position within 10 minutes. Other compositions are contemplated that contain an amount of enzyme capable of performing the same reaction to the same extent within 2 minutes.

The compositions contemplated by the present invention includes compositions in which the template independent polynucleotide enzyme present is a template independent polynucleotide polymerase. Examples of preferred template independent polynucleotide polymerases include TdTase and enzymes with similar activities.

The composition of the present invention includes a nucleoside having a removable blocking moiety protecting the 3' position of the nucleoside. Particularly preferred are nucleoside 5'-triphosphates having a removable blocking moiety protecting the 3' position of the nucleoside. The various useful removable blocking moieties are described herein.

In preferred compositions, the nucleoside having the removable blocking moiety protecting the 3' position is present at a concentration of 1 nanomolar to 100 mmolar. In other preferred compositions, the nucleoside is present at a concentration of 1 micromolar to 1 millimolar. In other preferred embodiments, the nucleoside 5'-triphosphate having the removable blocking moiety protecting its 3' position is present at a concentration of 10 times the Km of the enzyme present in the composition.

D. Automated Processes and Apparatus

The present invention contemplates the incorporation of the method described herein in an automated process in an apparatus and in devices. For example, the various buffer and reagent solutions of the inventive process can be provided to synthesis columns containing initiating substrates affixed to solid support matrices by the use of flexible tubing attached to peristaltic pumps or similar devices controlled by a microprocessor programmed to meter the exact quantities of the materials in the correct sequence.

Regardless of the equipment employed, it can be appreciated that the method of the present invention can create single phosphodiester bonds between desired nucleosides with very high efficiency and can potentially be used to produce long chain polynucleotides in high yields.

One example of such an automated process is depicted by a porous frit 13 in a glass or plastic vessel 15 shown in FIG. 3. The insoluble matrix 11 consists of a solid support such as cellulose, SEPHAROSE™ or CPG to which a nucleotide, nucleoside or polynucleotide is covalently linked at the 5'-position of the terminal nucleotide or to which an oligo- or poly- nucleotide or nucleoside having a terminal nucleoside with a free 3'-hydroxyl group is covalently attached via the 5'-hydroxyl group. The matrix II may itself be a covalent component of the porous frit 13 or it may be a separate entity.

The various solutions involved in the synthesis cycle are stored in stock containers 21, 23, 25, 27, 28 and 29. Solutions are introduced into the vessel 15 through tubes 41, 43, 47, 48, 49 and 50 attached to pumps 31, 33, 35, 37, 38, 39 and 40. The composition of the stock solutions would depend on the stability of the various components of the mixture. A simplified automated process would combine many of the various reagents as follows:

The stock containers 21, 23, 25 and 27 contain buffer solutions 51, 53, 55 and 57, respectively, having a concentration between about 10 and about 500 mM of sodium cacodylate (pH 7.0 at 25° C.), between about 0.1 and about 1.0 mM of dithiothreitol. Each buffer solution also contains between about 0.10 and about 200 units per μL of an enzyme (e.g. TdTase) suitable for phosphodiester bond formation. Buffer solution 51 in stock container 21 also contains between about 0.20 and about 200 μM of deoxyadenosine 5'-triphosphate having a blocked 3'-hydroxyl group. Buffer solutions 53, 55 and 57 in stock containers 23, 25 and 27, respectively, contain equivalent concentrations of deoxycytosine 5'-triphosphate, deoxyguanosine 5'-triphosphate and thymidine 5'-triphosphate respectively, each of which also has blocked 3'-hydroxyl groups. Buffer solution 58 in stock container 28 contains an appropriate reagent for deblocking the blocked 3'-hydroxyl groups of the four nucleosides as described previously. Stock solution 59 in stock container 29 contains a suitable neutralization buffer at pH 7.0, such as 0.1M sodium cacodylate. Stock solution 30 in container 60 contains a suitable enzymatic solution or chemical reagent for releasing the final product from the solid support as described previously.

The various stock solutions are drawn into the tubing, which each feed onto the matrix. Recycling of buffer solutions 51, 53, 55 and 57 from the vessel 15 to their respective stock containers 21, 23, 25 and 27 can be accomplished by way of the tubing 61, 63, 65 or 67. Allocation of fluid to the appropriate tubing can be accomplished by a distributor, 71, which directs the fluid from the vessel 15. Distributor devices, such as multiport stopcocks and fraction collectors are familiar to one of ordinary skill in the art. Movement of the liquid through tubing which is downstream from the distributor (e.g. 61, 63, 65, 67, 69, 73) can be accomplished by additional pumping as needed (e.g. pump 83, 85, 87, 89, 91, 93). At least one microprocessor controls the peristaltic pumps and distributor so as to provide for the sequential addition and recycling of the nucleotides to form a nucleotide chain having a predetermined nucleotide sequence. In the preferred processes, the initiating substrate linked to the matrix 11 is first exposed to one of the solutions 51, 53, 55, or 57 for a sufficient time to enable attachment of the nucleotide to the initiating substrate. This solution is then recycled into the appropriate container (21, 23, 25, or 27).

The amount of TdTase and 5'-nucleoside triphosphate contained in the buffer solutions 51, 53, 55 and 57 is sufficient for the synthesis of a predetermined quantity of an object nucleotide chain. For example, for the automated synthesis of 1 nmol of a nucleotide chain consisting of 1,000 bases (about 330,000 MW and about 330 μg), each buffer solution will contain an excess of each 5'-nucleoside triphosphate (about 500 nmol) and an excess of TdTase (about 100 to about 1,000 units). only a small fraction of the buffer solution containing the TdTase and the 5'-nucleoside triphosphate is used for each cycle of nucleotide addition. Matrix 11 is next exposed to solution 58 for a sufficient period of time to remove blocking groups from the growing oligo- or polynucleotide chain. This solution is not recycled but is distributed to tube 69 by the distributor 71, utilizing pump 91.

Matrix 11 is then briefly exposed to solution 59 in order to wash out the deblocking reagent. The next enzyme/nucleotide solution, either 51, 53, 55 or 57, is then added to matrix 11 to continue the cycle.

Finally, after the desire oligo- or polynucleotide is synthesized, cleavage of the object polynucleotide from the solid support occurs by the controlled addition of solution 60 which can be a restriction endonuclease solution or a solution to effect the chemical cleavage from the solid support (e.g., 1M piperidine) as described above. The microprocessor directs the distributor 71 and pump 93 to move the final product through tube 73 to be recovered for final workup.

As an example of the control of the various reactions by the microprocessor, the synthesis of the oligonucleotide ACGT onto an initiating substrate would involve the sequence of commands shown below. The duration of and between each command is sufficient to allow any particular reaction or fluid movement to proceed adequately.

| | Microprocessor Command | Intended Result |
| --- | --- | --- |
| 1. | Pump 31 on. | Solution 51 added to vessel 15 |
| 2. | Pump 31 off. | Nucleotide addition reaction proceeds |
| 3. | Distributor 71 on, pump 83 on. | Recycle reaction fluid fluid via tube 61 |
| 4. | Distributor 71 off, pump 83 off. | Solution 58 added to vessel 15; initiate deblocking reaction |
| 5. | Pump 38 off. | Deblocking reaction proceeds |
| 6. | Distributor 71 on, | Discard deblocking fluid via tube 69 |

| | Microprocessor Command | Intended Result |
|---|---|---|
| | pump 91 on. | |
| 7. | Pump 39 on. | Neutralize/wash reaction chamber |
| 8. | Distributor 71 off, pump 69 off, pump 33 on. | Solution 53 added to vessel 15 |

This cycle is repeated for the other nucleotides until the desired sequence is synthesized. When collection of the final product is desired, the microprocessor gives the following commands after step 7 above.

| 1. | Pump 40 on. | Solution 60 added to vessel 15 |
|---|---|---|
| 2. | Pump 40 off. | Cleavage reaction of the initiating substrate proceeds |
| 3. | Distributor 71 on, pump 93 on | Collection of synthesized DNA via tube 73 |

The alternative strategy envisions the use of immobilized nucleotide triphosphates in order to separate the object nucleotide from non-reacting substrate polynucleotides at every cycle. The automated process using immobilized nucleotide is considerably different from the process involving an immobilized substrate polynucleotide. After the coupling reaction of the triphosphate and the polynucleotide, the eluate contains unreacted polynucleotides, reaction buffer, and TdTase enzyme. The object polynucleotide is attached to the solid support. In order to recycle the enzyme back to its reservoir, the contaminating polynucleotide is first removed by passing the solution through a column containing hydroxyl apatite, for example, or a similar polynucleotide adsorption medium through which the enzyme will pass. This column will have sufficient capacity to adsorb all of the anticipated contaminating polynucleotides produced by every cycle.

After the deblocking step, the object polynucleotide is now contained in a solution of nucleotide triphosphates (with 3'-hydroxyls), and deblocking buffer (e.g., NaoH or phosphatase). These two contaminants can be removed by size exclusion chromatography (e.g., SEPHAROSE™ CL-6B) or by any of a number of commonly used techniques for separating small molecules from oligo- and polynucleotides. An example of this is adsorption of the object polynucleotide by annealing to oligo dA-cellulose column (3'-5') which would simply require the initiating substrate to contain oligo dT. A-T annealing is the preferred embodiment in the automated process since elution of the object polynucleotide can be accomplished by incubation with $H_2O$. The annealing of the object nucleotide simply requires the neutralization of the cleavage reaction by addition of a sufficient quantity of HCl or by the inclusion of an appropriate amount of NaCl (~0.1–0.5M) in the deblocking buffers.

An automated process incorporating the immobilized nucleotide triphosphate alternative method of the present invention is depicted in FIG. 4. The process utilizes a nucleotide triphosphate immobilized to a solid support by, but not limited to, techniques describe previously, and compromising stock solutions 151, 153, 155, 157 in stock containers 121, 123, 125, 127. The stock solutions contain a tethered nucleotide, appropriate buffers and sufficient enzyme to effect the synthesis of the desired amount of predetermined sequence. The immobilization material has fluid dynamic properties allowing it to be moved through the various tubes as required. Substances which have these characteristics (e.g. gels and viscous suspensions) are familiar to one of ordinary skill in the art. The reaction vessel, 115, contains a reaction chamber, 111, and a stopcock, 113. Stopcock 113 has three positions A, B, C. Position A aligns a hole of sufficient diameter with the tubing so as to allow the various components of the synthesis to pass unimpeded. Position B aligns a porous frit to which is covalently attached oligonucleotides of deoxyadenosine (dA) approximately 20 bases in length. The quantity of oligo dA is sufficient to anneal the entire quantity of oligo dT, attached to the initiating substrate as described above. In position B, only solutes can pass through and no immobilization material (e.g. those contained in solutions 151, 153, 155, 157). Position C closes all flow. Reaction chamber 111 contains the initiating substrate in water, solution 161. As mentioned above the initiating substrate contains oligo dT which is $\geq 20$ nucleotides in length. Stock containers 121, 123, 125, 127, 128 and 129 are connected to the reaction vessel 115 by way of peristaltic tubing or some similar material to effect transport of the reagents contained in the stock containers. Additionally, vessel 115 is connected to tubing, 181, which contains a distributor, 171 which serves to divert the flow of solutes either to tubing 183 or tubing 185 or recycled back to stock containers after passing through adsorption media (e.g. hydroxylapatite) contained in 130, 132, 134 or 136 via tubes 187, 189, 191 or 193. Tubing 183 feeds back to vessel 115; tubing 185 feeds into a discard container. Solute movement through the tubing is facilitated by pumps, 131, 133, 135, 137, 138, 139, 163 (e.g. peristaltic pumps) or similar devices which will force fluids, gels or viscous suspensions through tubing to desired destinations.

The automated process for synthesis involves the following flow of solutes and stopcock positions controlled by at least one microprocessor. The microprocessor controls pumps, the distributors and the stopcock positions:

1) Stopcock 113, position C (blocked); stopcock 171 in discard position (tube 185); tethered nucleotide, buffers (solution 151, 153, 155, or 157) are combined with substrate oligonucleotide or polynucleotide (solution 161) to yield a tethered oligonucleotide or polynucleotide.

2) Stopcock 113, position B (oligo-dA frit); distributor 171 in recycle position (tube 187, 189, 191 or 193); unreacted polynucleotide is adsorbed in containers 130, 132, 134 or 136; enzyme, buffers are recycled.

3) Stopcock 113, position B (oligo-dA frit); stopcock 171 in discard position (tube 185); cleavage buffer (solution 158) added to immobilized polynucleotide yielding a free polynucleotide annealed to the oligo-dA frit; released mononucleotides discarded.

4) Stopcock 113, position B (oligo-dA frit); stopcock 171 in recycle position (tube 183); water (solution 159) is passed through the chamber and frit to release the annealed polynucleotide from the frit and return the polynucleotide to the reaction chamber. The free polynucleotide resides in tubing 183 during Step 5.

5) Stopcock 113, position A (completely open); stopcock 171 in discard position (tube 185); immobilized substrate discarded prior to entry of polynucleotide back into reaction chamber.

6) The final product is recovered via tube 185 with stopcock 113 in position A.

It will be appreciated that for these separation techniques to be effective, the starting oligonucleotide or polynucleotide substrate should consist of at least approximately 20 nucleotides. The composition of the starting oligonucleotide or polynucleotide can be anything that will enable the subsequent purification steps as well as the ultimate cleavage of the object oligonucleotide or polynucleotide from the starting oligo- or polynucleotide. An example of a nucleotide modification that would enable final separation of starting oligonucleotide or polynucleotide from the object polynucleotide is biotinylation of the primary amines of dA, dC, or dG. Additionally, a starting oligonucleotide substrate containing 7-methyl guanosine at the 3' end will provide a cleavage site, as described previously, for ultimate recovery of the object polynucleotide.

Thus, it can be appreciated that, regardless of the equipment employed, the method of the present invention efficiently produces oligonucleotide or polynucleotides in high yield, with a significant reduction in the number of unreacted sequences per cycle. This greatly simplifies the ultimate isolation of the object nucleotide chain for further experimentation. Once isolated, the nucleotide chain may be "stitched" together with other polynucleotides and formed into double stranded DNA as described above or may be amplified by conventional means such as by polymerase chain reactions for use in recombinant DNA end use applications.

E. Kits

The present invention also contemplates a kit for carrying out the present inventive procedure. Typically, a kit would contain all the solutions and substances needed for performing the instant synthesis procedure together with instructions for carrying out the procedure. A typical kit for carrying out the claimed process would include an initiating substrate of the present invention, various nucleoside 5' triphosphates of the present invention having a removable blocking moiety protecting the 3' position, an enzyme of the present invention capable of catalyzing the formation of a 5' to 3' phosphodiester linkage between the unprotected 3' hydroxyl group of the initiating substrate and the 5' phosphate of the blocked 5'-triphosphate. Additional components and solutions optionally included in the kit are various required reaction solutions and reaction buffers, reaction vessels in which to perform the assay, deblocking chemicals, solutions or enzymes of the present invention.

A kit for carrying out the instant synthesis may also contain initiating substrates that are attached to a solid support. The kit may contain a variety of initiating substrates attached to solid supports, so that the first nucleoside of a desired oligonucleotide can be selected by selecting the appropriate initiating substrate.

In other kits for carrying out the present process, initiating substrates having oligonucleotides of a preselected nucleotide sequence are provided to allow oligonucleotides and polynucleotides having this preselected nucleotide sequence incorporated into its 5' to be produced. Kits with this type of initiating substrate can provide easy synthesis of oligonucleotides having, for example, a restriction endonuclease cleavage site present in its nucleotide sequence.

Other kits contemplated by the present invention include initiating substrates having various derivatized nucleotides, nucleoside analogs, or non-nucleoside molecules that allow oligonucleotides produced using those initiating substrates to have useful properties such as easily coupling to other molecules, unique biologic activity or other unique features. Other kits would have an initiating substrate of the present invention such as double-stranded oligonucleotides.

The present invention also contemplates kits for producing nucleoside 5'-phosphate and nucleoside analogs having a removable blocking moiety protecting its 3' position. These kits would allow a user to produce nucleoside 5' triphosphates and equivalents that are useful in the practicing of the present invention.

The present invention also contemplates kits that contain additional components for carrying out other molecular biologic procedures in conjunction with the methods of the present invention. For example, components of the present invention may be present in a kit that contains vectors and concomitant cell lines for expression of a protein or enzymes for desired modifications of amplification of the nascent or fully synthesized object polynucleotide.

The following examples further illustrate the present invention, and are not to be construed as limiting the scope thereof. Unless otherwise indicated, materials were obtained from Promega, Fisher, Aldrich, Sigma, Pharmacia, Gibco-BRL, Bio-Rad and New England Biolabs. All parts and percentages are by weight unless expressly indicated to be otherwise, and all temperatures are in degrees Celsius.

EXAMPLES

Example 1. Synthesis of Protected Nucleotides
A. Synthesis of Protected Nucleotides by Reaction of the 3' Hydroxyl with Carboxylic Acids i. Toluic acid. One hundred μL of 1M toluic acid (either the para or ortho isomer) in anhydrous N,N-dimethylformamide (DMF) was mixed, in a nitrogen atmosphere, with 100 μL of 1M carbonyldiimidazole, also in anhydrous DMF. Formation of the imidazolide was allowed to proceed at room temperature for 30 seconds. To this mixture was added 100 μL of a 50 mM solution of deoxynucleoside 5'-triphosphate in water. Formation of the toluoyl-dNTP ester proceeded at room temperature for 12 hours.

The triphosphates (including both 3'-hydroxy unreacted triphosphates and the 3'-toluoyl triphosphates) were separated from the other reaction components by precipitation in the presence of 9 volumes of acetone. The insoluble nucleoside triphosphates were recovered by centrifugation and removal of the soluble components. The nucleosides were then redissolved in 100 μL of water, toluoyl ester was separated from the starting nucleotide by chromatography on Whatman 3 MM cellulose paper which had been pre-washed first in isopropanol, butanol, and water in the proportion of 2:2:3 by volume, and then in water alone, prior to drying. The solvent to achieve separation by ascending chromatography contained isopropanol, butanol, and water also in the proportion of 2:2:3 by volume. Detection of the various separated components was by ultraviolet light absorption at 254 nm. The dNTP-3'-O-toluate was cut from the paper and eluted into water. After concentration to dryness in vacuo, the nucleotide ester was redissolved in water to a final concentration of ~0.1–1 mM. This material was then subjected to mass spectroscopic analysis to confirm the structure. The predicted mass numbers for the toluoyl esters of dATP, dCTP, dGTP, and TTP are 608, 584, 624, and 599 respectively. In each case these mass numbers were observed. These mass numbers were not observed in the spectra obtained from the unprotected deoxynucleoside triphosphates.

In related experiments, a variety of esters have been formed from carboxylic acids to yield aromatic or aliphatic protecting groups at the 3' position.

ii. Benzoic acid and dimethylbenzoic acid. Benzoic acid as well as the 2,6- and 3,5-dimethylbenzoic acid isomers were esterified to nucleotide triphosphates by the same methods described above in order to evaluate position effects of methyl groups on the overall kinetics of subsequent enzyme reactions.

iii. 4-Nitrobenzoic acid. Esterified to the 3'-hydroxyl using the same methods.

iv. 2-Napthoic acid. Esterified to the 3'-hydroxyl using the same methods.

v. Isovaleric acid. Esterified to the 3'-hydroxyl using the same methods.

Depending on the particular stability requirements, the procedures are readily adaptable to the utilization of virtually any carboxylic acid for esterification and protection of the 3'-hydroxyl of a nucleotide triphosphate.

B. Synthesis of Protected Nucleotides by Reaction of the 3'-hydroxyl with an Ether 2.5 mg of deoxynucleoside triphosphate was dissolved in 100 µL anhydrous DMSO containing 5.2 mg para-toluene sulfonic acid. The solution was cooled to 0° C.; 200 µL of ethyl vinyl ether was then added and allowed to react for 3 minutes. 200 µL of 1M Tris-Cl, pH 9.0 was then added with vigorous shaking resulting in the formation of two liquid phases. The ether phase was discarded and to the aqueous phase was added 10 volumes of absolute ethanol to precipitate the nucleotides. After incubation for 10 minutes at −20° C. the nucleotide pellet was obtained by centrifugation, and was redissolved in 0.25M NaCl followed by the addition of 10 volumes of ethanol. The final precipitated nucleotide pellet was dissolved in 100 µL of water and applied to Whatman 3 MM paper for chromatography to separate the nucleotide ether from unreacted nucleotides. Ascending chromatography was performed as described above with a solvent of isopropanol, butanol, and water in the proportion of 2:2:3 by volume. The nucleotide ether, where the protecting group is an ethoxyethyl moiety, migrates with an $R_f$ (relative to the unreacted nucleotide) of 1.25. This species was cut out of the paper and eluted with water to yield the purified derivative.

C. Synthesis of Protected Nucleotides by Phosphorylation of the 3'-hydroxyl i. Chemical synthesis. 2.0 mg of deoxynucleoside triphosphate was dissolved in 60 µL anhydrous DMSO, 2 µL orthophosphoric acid, and 6 µL triethylamine. To start the reaction, 6 µL of trichloroacetonitrile was added and the mixture was incubated at 37° C. for 30 minutes. The reaction was cooled to room temperature and 5 µL of 5M NaCl was added followed by 1.4 mL of acetone. The precipitation of nucleotide was allowed to proceed at −20° C. for 10 minutes; nucleotide was recovered by centrifugation, redissolved in 100 µL 0.25M NaCl and reprecipitated by the addition of 1.4 mL of absolute ethanol. The final nucleotide was recovered by centrifugation, dissolved in 100 µL of water and applied to Whatman 3 MM paper. Separation of nucleotide tetraphosphate (5'-triphosphate, 3'-monophosphate) was by ascending chromatography in isopropanol, butanol, and water in the proportion of 2:2:3 by volume. The nucleotide tetraphosphate migrates with an $R_f$ (relative to the unreacted nucleotide) of 0.90.

Alternatively, the same phosphorylation reaction components (phosphoric acid, teithylamine, and deoxynucleotide) can be dissolved in formamide and the reaction allowed to proceed at 70° C.

Alternative chromatography solvents include 1-propanol, concentrated ammonia, water (55:20:25), in which case the Rf of the tetraphosphate or 3 mm paper is approximately 0.8 relative to unreacted triphosphate.

ii. Enzymatic synthesis. Deoxynucleoside 3'-monophosphates (Sigma) were phosphorylated at the 5' position using polynucleotide kinase. The reaction was performed at pH 9.0 to minimize the inherent 3' phosphatase activity of the enzyme, in a solution consisting of 50 mM Tris-Cl (pH 9.0), 10 MM $MgCl_2$, 1.5 mM spermine, 5 mM dithiothreitol, 3 mM 3'-dNMP, 30 mM ATP, and 20 units of polynucleotide kinase (Sigma or Pharmacia) in a final volume of 200 µL for 16 hours at room temperature. The phosphorylation was monitored by chromatography (Whatman 3 MM paper) after removal of the ATP by chromatography through Affi-Gel 601 (Bio-Rad).

The nucleoside 5'-monophosphate 3'-monophosphate was further phosphorylated at the 5' position using nucleoside monophosphate kinase and pyruvate kinase in a solution containing 50 mM Tris-Cl (pH 7.4), 10 mM $MgCl_2$, 1.5 mM spermine, 5 mM dithiothreitol, 30 mM ATP, 4 mM phosphoenolpyruvate, 10 mM KCl 150 µg/mL pyruvate kinase (Sigma), and 100 µg/mL nucleoside monophosphate kinase (Boehringer Mannheim). The reaction proceeded at room temperature for 30 minutes (for dA) to 4 hours (for dT, dC, dG). The deoxynucleotides were again separated from ATP by chromatography on Affi-Gel 601 followed by concentration to dryness in vacuo and dissolution in 200 µL of water. Purification of the tetraphosphate from other nucleotides was by paper chromatography as described above.

D. Synthesis of a Benzoylated Nucleotide Tethered to Agarose Beads

One hundred µL of 1M p-aminobenzoic acid in 10 mM sodium hydroxide, 90% DMF, pH 10, was mixed with 100 µL of 1M N-succinimidyl 3-(2-pyridylthio)propionate also in basic DMF. Coupling of the succinimidyl to the amine was allowed to proceed at room temperature for four hours. The reaction was monitored and the coupled product purified by thin layer chromatography on silica gel using a mixture of chloroform and methanol as the solvent. Silica gel containing the coupled product was extracted with DMF, filtered, and added to an equal volume (~100 µL) of 1M carbonyl diimidazole in anhydrous DMF followed immediately by the addition of 100 µL of 50 mM deoxynucleoside triphosphate. The product, a dNTP coupled by an ester linkage to a tether containing an amide and a disulfide bond, was treated with 2-mercaptoethanol in a nitrogen atmosphere to expose the sulfhydryl, and subsequently purified by purification from 10 volumes of absolute ethanol. The purified product, under nitrogen atmosphere, was then incubated with 0.2 mL Affi-Gel™ 501, an organomercurial crosslinked agarose, in 50 mM sodium phosphate, pH 6, at room temperature for one hour to allow covalent mercaptide bonds to form.

E. Production of Nucleoside Having a Removable 3' Blocking Moiety Using Alternate Strategies An alternative strategy for making ester and ether triphosphates involves chemical phosphorylation of a nucleoside which already contains an ester or ether protecting group at the 3' position.

Isovaleroyl Ester. One hundred µL of 1M isovaleric acid dissolved in anhydrous N,N-dimethylformamide (DMF) under a nitrogen atmosphere is mixed with 100 µL of 1M carbonyldiimidazole, also in anhydrous DMF. Formation of the imidazolide is allowed to proceed at room temperature for 30 seconds. To this mixture is added 100 µL of 5'-O-dimethoxytrityl thymidine (DMT thymidine; Sigma Chemical Co.) also dissolved in anhydrous DMF. Formation of the isovaleroyl ester at the 3' hydroxyl proceeds at room temperature for 12 hours.

The 5'-DMT 3'-isovalerate thymidine is purified by thin layer chromatography or HPLC and recovered from solvents in vacuo. To remove the 5' protecting group, the compound is reacted in 1 mL of methylene chloride with 5 equivalents of finely powdered, anhydrous zinc bromide with stirring at room temperature. The reaction is monitored by TLC to determine the optimum time for specific removal of the DMT group. The 5'-OH 3'-isovaleroyl ester of thymidine is then recovered after TLC or HPLC purification. These procedures are generally applicable to all four nucleosides.

To phosphorylate the 5' hydroxyl, the ester is dissolved or resuspended on 0.5 ml triethyl phosphate. 0.4 mmol phosphoryl chloride ($POCl_3$) is added and the reaction is allowed to proceed at room temperature for 1–14 hours. Purification of the 5'-monophosphate-3'O-isovaleroyl ester is by chromatography on DEAE Sephadex A-25 eluted with a linear gradient of triethylammonium carbonate (pH 7–8). The monophosphates are eluted at a buffer concentration of approximately 0.2–0.3M.

The purified monophosphate ester (0.1 mmol) is converted into its pyridinium salt with the pyridinium form of Dowex-50W X-8 cation exchange resin. The tributylammonium salt is prepared by addition of tributylamine (0.2 mmol), and the product is dried by addition and evaporation of anhydrous pyridine and N,N-dimethylformamide. To a solution of the anhydrous tributylammonium salt in N,N-dimethylformamide (1 ml) is added 1,1-carbonylbis (imidazole) (0.5 mmol). Formation of the imidazolide may be monitored by TLC chromatography or HPLC. After the reaction is complete, 35 µL of methanol is added to react with remaining carbonylbis(imidazole) and the solution is kept at room temperature for 5 minutes. Tributylammonium pyrophosphate (0.5 mmol) in N,N-dimethylformamide (5 ml) is then added dropwise with stirring. The mixture is kept for several hours at room temperature then evaporated to dryness. The triphosphate is isolated by chromatography as above and is eluted at approximately 0.4–0.5M triethylammonium carbonate buffer. These phosphorylation procedures are generally applicable to all four nucleosides.

Depending on the particular stability requirements, the procedures described above are readily adaptable to the utilization of virtually any carboxylic acid for esterification and protection of the 3'-hydroxyl followed by the chemical phosphorylation of the 5' hydroxyl to produce the 3' protected nucleotide triphosphate. These carboxylic acids include but are not limited to the following classes: formic, benzoylformic, chloroacetic, fluoroacetic, methoxyacetic, phenoxyacetic, chlorophenoxyacetic, phenylacetic, propionic, butyric, isovaleric, succinic, pentanoic, pivalic, adamantane carboxylic, crotonic, butenoic, substituted benzoic (e.g. nitrobenzoic, methylbenzoic, chlorobenzoic, phenylbenzoic), napthoic acids.

As is understood by those of ordinary skill in the art, there are numerous methods for creating esters for the purpose of transiently protecting hydroxyl groups. In addition, there are numerous strategies for transiently protecting one hydroxyl group (e.g. the 5' hydroxyl of a nucleoside) in order to introduce an ester at another hydroxyl group (e.g. the 3' hydroxyl of a nucleoside).

Silyl Ether. 1 mmol of thymidine is dissolved in 1 ml of N,N-dimethylformamide at room temperature. To this solution is added 20 mmol of imidazole and 10 mmol of tert-butyldimethylsilylchloride (t-BDMS). The reaction is allowed to proceed at room temperature until both hydroxyl groups are silylated.

The disilylated nucleoside is recover by TLC or HPLC and the solvents removed in vacuo. The 5' silyl protecting group is then selectively removed by incubation in 80% acetic acid. The reaction is monitored by TLC to determine the optimum time for removal of the 5' protecting group. The resulting 3' silylated nucleoside is purified by TLC or HPLC, phosphorylation at the 5' position is by the procedures described above yielding a nucleotide triphosphate 3'-t-BDMS ether. These procedures are generally applicable to all four nucleosides.

Methoxymethyl Ether. 1 mmol of DMT-thymidine is dissolved in diisopropylethylamine and reacted with 4 mmol chloromethyl methyl ether (Aldrich Chemical Co.) at 0° C. for 1 hour followed by warming to room temperature and further reaction for 8 hours. The thymidine 5'-DMT 3'-methoxymethyl ether is purified by TLC or HPLC and recovered from solvents in vacuo.

To remove the 5' protecting group, the compound is reacted in 1 mL of methylene chloride with 5 equivalents of finely powdered, anhydrous zinc bromide with stirring at room temperature. The reaction is monitored by TLC to determine the optimum time for specific removal of the DMT group. The 5'-OH 3'-methoxymethyl ether of thymidine is then recovered after TLC or HPLC purification. Phosphorylation at the 5' position is accomplished by the procedures described above yielding a nucleotide triphosphate 3'-methoxymethyl ether. These procedures are generally applicable to all four nucleosides.

As is understood by those of ordinary skill in the art, there are numerous methods for creating ethers for the purpose of transiently protecting hydroxyl groups. In addition, there are numerous strategies for transiently protecting one hydroxyl group (e.g. the 5' hydroxyl of a nucleoside) in order to introduce an ether at another hydroxyl group (e.g. the 3' hydroxyl of a nucleoside).

Ethers useful for protection of nucleoside 3' hydroxyl groups include but are not limited to the following classes: methyl, substituted methyl (e.g. benzyloxymethyl, methoxyethoxymethyl, trimethylsilyl ethoxymethyl), pyranyl, furanyl, sustituted ethyl (e.g. ethoxyethyl, methoxyethyl, methylmethoxy ethyl), butyl, allyl, cinnamyl, benzyl and substituted benzyl (e.g. methoxybenzyl, halobenzyl, nitrobenzyl), anthryl and silyl ethers.

Example 2. Regeneration of the 3' Hydroxyl from Protected Nucleotides

A. Deprotection of nucleotide 3'-O esters. The ester protecting groups were removed from the 3'-hydroxyl of dNTPs by incubation in 1 mM $CoCl_2$ and 100 mM potassium cacodylate, pH 6.8. The conversion of the ester to the hydroxyl was evaluated by cellulose and paper chromatography and was found to be nearly quantitative after 15 minutes of incubation at 37° C. These deprotection conditions were equally effective for each of the four nucleotides. Further evaluation revealed that the instability was due to both the buffer and the divalent cation.

The instability of the toluoyl esters in other commonly used TdTase coupling reaction buffers was explored. The relative degree of instability due to the various buffers (in the presence of 1 mM $COCl_2$) was found to be cacodylate>tris (hydroxymethyl) aminomethane>sodium acetate or phosphate. Instability due to the cations (in cacodylate buffer) was found to be $Co^{++}$>$Mn^{++}$>$Mg^{++}$. Degradation of the esters was first observable after about three minutes of incubation. Incubation in buffer alone or cation alone produced no observable degradation. In common with many other types of esters, these deoxynucleotide esters were also sensitive to basic conditions e.g. incubation in 10–100 mM NaOH. The other esters of dNTPs (isovaleroyl, dimethylbenzoyl, napthoyl, and nitrobenzoyl) were also relatively unstable in the buffered divalent cations.

In general, these results identify unexpected properties of the esters of dNTPs and provide a convenient and gentle method for the rapid removal of these esters from the growing polynucleotide chain after a coupling reaction. These deprotection conditions are sufficiently gentle to enable the synthesis of an object polynucleotide onto a pre-existing double stranded DNA without denaturation of the DNA at every cycle. This capacity for "add-on" synthesis using a double-stranded polynucleotide as the initiating substrate is demonstrated in Example 5 below.

B. Deprotection of nucleotide 3'-O ethers. The 3' ethoxy ethyl ether of the nucleoside triphosphates were stable in cobalt containing buffers but could be readily removed by incubation in 5% acetic acid at room temperature or by incubation in 0.5N HCl/THF at 0° C.

C. Deprotection of nucleotide 3'-phosphates. The 3'-phosphate was specifically removed by incubation of the nucleotide in a solution containing 50 mM sodium acetate, pH 5.5, 10 mM $MgCl_2$, and 20 units of nuclease P1, an enzyme which specifically removes phosphates from the 3' position of mononucleotides. The reaction was allowed to proceed for 90 minutes at 37° C. This enzyme would not be appropriate in the case of a protected nucleotide attached to an initiating substrate since it is also a phosphodiesterase. In this case an alternative phosphatase can be used, which is described below.

Example 3. Efficiency of Enzyme Catalyzed Phosphodiester Bond Formation Using Protected Deoxynucleotidyl Triphosphates The ability of a polymerizing enzyme, TdTase, to catalyze the creation of a phosphodiester bond between an initiating polynucleotide substrate and a 3'-O-protected deoxynucleotidyl triphosphate was measured using a transferase/ligase assay. In this assay, transfer of a nucleotide to an initiating substrate DNA, such as a linearized vector, will inhibit the ability of the vector to be relegated into a circular form. The relative quantity of circular vector DNA in each reaction can then be measured by bacterial transformation.

100 $\mu$M deoxynucleotide 3' ethoxy ethyl ether, or 3' phosphate were incubated with Pst 1-digested Puc 8 vector DNA (1 $\mu$g) in the presence of 1 mM $CoCl_2$, 0.1 mM DTT, potassium cacodylate, pH 6.8, and 40 units TdTase (Promega) in a total volume of 25 $\mu$L. In the case of the 3' ester, the same reaction was performed with the exception that the CoCls was replaced with MnCl2 and the cacodylate buffer was replaced with Tris-Cl. The reactions were allowed to proceed at 37° C. for 15 minutes at which time they were terminated by the addition of 1 $\mu$L of 100 mM $Na_2$EDTA, 0.1% sodium dodecyl sulfate. The Puc 8 DNA was separated from the other components of the reaction by chromatography through aqueous packed Sepharose™ CL-6B and was then used in a ligase reaction. The ligation reaction consisted of the Puc 8 DNA, 1 mM $Na_2$ATP, 50 mM Tris-Cl, pH 8.0, 1 MM $MgCl_2$, 100 $\mu$g/mL bovine serum albumin and 100 units of T4 DNA ligase (New England Biolabs). The ligation reaction was allowed to proceed at 16° C. for 18 hours. The Puc 8 DNA was again recovered by Sepharose™ CL6B chromatography.

The inhibition of the ligation reaction due to the addition of a nucleotide to the Puc 8 DNA by TdTase was quantified by a bacterial transformation assay. Competent *E. coli* JM109 bacteria (Promega) were incubated with 100 ng of the Puc 8 DNA according to the instructions provided with the transformation competent cells. Briefly, this involved a heat shock of the admixture for one minute at 42° C., incubation of the bacteria in LB broth at 37° C. for one hour, and overnight growth of the bacteria on LB agar Petri plates containing 50 $\mu$g/mL ampicillin. Colonies from each transformation were then counted.

| dNTP in TdTase Reaction | Vector Substrate | Religation formed | Trans-Colonies |
|---|---|---|---|
| none (positive control) | Pst 1–Puc 8 | yes | 1,381 |
| none (background) | " | no | 325 |
| dideoxy-ATP | " | yes | 342 |
| dATP 3'-O toluate | " | yes | 316 |
| dATP 3'-O ether | " | yes | 330 |
| dATP 3'-phosphate | " | yes | 340 |
| dATP-3'OH | " | yes | 636 |

The results demonstrate that the protected nucleotides are utilized by TdTase for the creation of phosphodiester bonds. The covalent attachment of the protected nucleotide to the vector DNA blocks the vector from religation. In the case of the unprotected nucleotide (dATP 3'-OH) the enzyme may be predominantly adding homopolymer tails to a population of vector molecules leaving some vectors unmodified.

The efficiency of the TdTase catalyzed transfer, as measured by the numbers of colonies in excess of the background value, were comparable when comparing the protected mononucleotide with dideoxynucleotide. The absence of transformed colonies above the background value compared to a control which produced greater than 1000 colonies, indicates a TdTase catalyzed transfer of protected mononucleotide to >99.9% of the initiating substrate 3' hydroxyls.

Example 4. Inhibition of Phosphodiester Bond Formation by Protected Nucleotides Attachment of a protected mononucleotide to vector DNA will prevent the subsequent attachment of a biotin labelled nucleotide so long as the protecting group is affixed to the 3'-hydroxyl. This inhibition of vector biotinylation can be readily quantified by blotting assays after agarose gel electrophoresis.

Vector DNA (either Puc 8 or pBluescript) digested with the appropriate restriction enzyme, was reacted with approximately 100 $\mu$M protected nucleotide for varying times in the presence of 25 units TdTase (Promega or BRL) in appropriate buffers in a final volume of 25 $\mu$L. To the reaction mix was then added 1 $\mu$L of 300 $\mu$M biotinylated dUTP (Sigma or Boehringer) and the reaction was allowed to proceed for 1–3 minutes at which point the reaction was stopped by the addition of 1 $\mu$L of 1% sodium dodecylsulfate, 50 mM $Na_2$EDTA. The mixture was heated to 75° C. for 1 minute then electrophoresed in an agarose gel to visualize the DNA. In related assays, the vector DNA was purified from the other components of the reaction prior to the addition of biotinylated nucleotide. Purification was by centrifugal chromatography on Sepharose CL-6B. This step was included to avoid the possibility that low molecular weight inhibitors were slowing the activity of the TdTase.

The incorporation of biotin into the DNA was measured using a standard dye reaction procedure. The DNA was first blotted onto a piece of nitrocellulose paper. The nitrocellulose paper with the DNA adhering to it was then heated to 80° C. in a drying oven for 30 minutes and re-wetted in 25 mL of 50 mM Tris-Cl pH 8.1, 150 mM NaCl, 0.1% Triton-X-100 (TBST) and 10% (w/v) Carnation non-fat dry milk, a solution which is intended to enhance the contrast of the final dye reaction. After 1 hour of incubation in the milk solution, a fresh solution of TBST containing approximately 1 μg/mL of streptavidin alkaline phosphatase (Fisher Scientific #OB5000-ALPH) was added to the paper. Binding of streptavidin to biotin proceeded for 1 hour at room temperature. The paper was then transferred to 25 mL of fresh TBST for 10 minutes to wash off excess streptavidin-alkalin phosphatase. This washing step was repeated four times. The paper was then transferred to 10 mL of 100 mM Tris-Cl, pH 9.5, 150 mM NaCl, 5 mM MgCl2, 300 μg/mL nitrotetrazolium blue and 150 μg/mL bromochloroindolyl phosphate to visualize the quantity of bound streptavidin phosphatase by enzymatic release of the chromophoric bromochloro indole.

The results of the inhibition assays using a variety of blocking groups is summarized below.

| 3' protecting group (%) | Biotinylation time (min) | Reaction time (min) | Inhibition |
|---|---|---|---|
| para-toluoyl | 0.5–5 | 0.5–5 | >50% |
| benzoyl | " | " | " |
| isovaleroyl | " | " | " |
| dimethylbenzoyl | " | " | " |
| ethoxyethyl | " | " | " |
| phosphate | " | " | " |

Example 5. DNA Synthesis Using Protected dNTPs: Synthesis of a New Restriction Site in the Puc 8 Vector To demonstrate the synthesis of a desired DNA sequence directly onto a vector DNA by the TdTase catalyzed addition of the protected dNTPs, we performed sequential reactions on Pst 1-digested Puc 8 DNA in order to introduce a new restriction site into the vector. The sequence at the termini of the Pst1 Puc 8 DNA is:

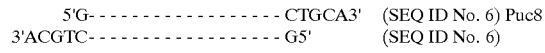
5'G- - - - - - - - - - - - - - - - - CTGCA3'    (SEQ ID No. 6) Puc8
3'ACGTC- - - - - - - - - - - - - - - - G5'      (SEQ ID No. 6)

where the dotted lines indicate the annealed complementary strands of the vector. Sequential coupling and cleavage reaction were performed using the toluoyl esters of dNTPs as follows:

First coupling reaction—100 mM potassium cacodylate, pH 6.8, 1 mM CoCl2, 0.1 mM DTT, 0.1 mg/mL BSA, 100 μM dTTP-3'O-toluate, 40 units TdTase (Promega), 37° C., 2 minutes.

Stop reaction—1 μL 100 mM Na2EDTA, 1 μL 10% sodium dodecyl sulfate, 65° C., 2 minutes.

DNA recovery—Centrifugation through 0.5 mL packed Sepharose™ CL-6B in water.

Ester cleavage reaction—100 mM potassium cacodylate, pH 6.8, 1 mM CoCl2, 0.1 mM DTT, 0.1 mg/mL BSA, 37° C., 30 minutes.

Second coupling reaction—100 μM dGTP-3'O-toluate, 40 units TdTase (Promega), 37° C., 2 minutes.

Repeat stop, recovery and cleavage.

Third coupling reaction—100 μM dCTP-3'O-toluate, 40 units TdTase (Promega), 37°C., 2 minutes.

Repeat stop, recovery and cleavage.

Fourth coupling reaction—100 μM dATP-3'O-toluate, 40 units TdTase (Promega), 37° C., 2 minutes.

Repeat stop, recovery and cleavage.

Final recovery of DNA—Centrifugation through 0.5 mL packed SEPHAROSE™ CL-6B in water.

A similar series of reaction were performed using the 3'-phosphates of the dNTPs with some modifications.

First coupling reaction—100 mM potassium cacodylate, pH 6.8, 1 mM CoCl2, 0.1 mM DTT, 0.1 mg/mL BSA, 100 μM dTTP-3'-phosphate, 40 units TdTase (Promega), 37° C., 2 minutes.

Stop reaction—1 μL 100 mM Na2EDTA, 1 μL 10% sodium dodecyl sulfate, 65° C., 2 minutes.

DNA recovery—Centrifugation through 0.5 mL packed SEPHAROSE™ CL-6B in water.

Phosphate cleavage reaction—0.1m Tris.Hcl, pH 9.0, 0.1m Nacl, 10 mM MgCl2, and 20 units of alkaline phosphatase, 37° C., 30 minutes.

Second coupling reaction—100 μM dGTP-3'-phosphate, 40 units TdTase (Promega), 37° C., 2 minutes.

Repeat stop, recovery and cleavage.

Third coupling reaction—100 μM dCTP-3'-phosphate, 40 units TdTase (Promega), 37° C., 2 minutes.

Repeat stop, recovery and cleavage.

Fourth coupling reaction—100 μM dATP-3'phosphate, 40 units TdTase (Promega), 37° C., 2 minutes.

Repeat stop, recovery and cleavage.

Final recovery of DNA—Centrifugation through 0.5 mL packed SEPHAROSE™ CL-6B in water.

The modified vector DNA was intended to have the following new DNA sequence:

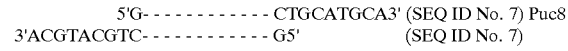
5'G- - - - - - - - - - - - CTGCATGCA3' (SEQ ID No. 7) Puc8
3'ACGTACGTC- - - - - - - - - - - G5'    (SEQ ID No. 7)

To demonstrate the presence of this new sequence in the vector, the modified Pst 1-Puc 8 was religated as previously described for 18 hours at 16° C. The resulting recircularized or concatemerized plasmid would have the following new structure in the Puc 8 polylinker:

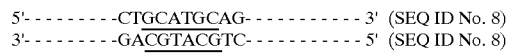
5'- - - - - - - - -CTGCATGCAG- - - - - - - - - - -3' (SEQ ID No. 8)
3'- - - - - - - - -GA<u>CGTACG</u>TC- - - - - - - - - - -5' (SEQ ID No. 8)

where the underlined portion is the recognition sequence for the Sph 1 restriction enzyme, which did not previously exist in the vector.

The relegated vector was passed through a CL-6B spun column and incubated in the Sph 1 restriction enzyme buffer and 10 units of Sph 1 (New England Biolabs). Agarose gel electrophoresis revealed that the original Puc 8 DNA contained no Sph 1 recognition sequences and that the recovered DNA after the TdTase reactions contained the desired sequence.

To demonstrate the significance of the blocking groups, an identical protocol was followed using unblocked nucleotide triphosphates in the synthesis reactions. The final religation product contained no detectible Sph 1 sequences.

The foregoing examples and description of the preferred embodiment should be taken as illustrating, rather than as limiting, the present invention as defined by the claims. As will be readily appreciated, numerous variations and combinations of the features set forth above can be utilized without departing from the present invention as set forth in the claims. All such modifications are intended to be included within the scope of the following claims.

We claim:

1. A mononucleoside 5'-triphosphate having a removable blocking moiety protecting the 3' position which is an ether and which has the following formula:

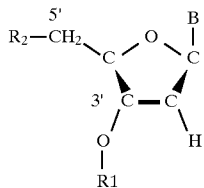

wherein $R_2$ is a triphosphate group and $R_1$ is selected from the group consisting of methyl, $CH_3(CH_2)_N$, wherein N is an integer from 1–10, methoxymethyl, methylthiomethyl, benzyloxymethyl, t-butyoxymethyl, 2-methoxyethoxymethyl, 2,2,2-trichloroethoxymethyl, bis(2-chloroethoxy)methyl, 2-(trimethylsilyl)ethoxymethyl, tetrahydropyranyl, 3'-bromotetrahydropyranyl, tetrahydrothiopyranyl, 4'-methoxytetrahydropyranyl, 4'-methoxytetrahydrothiopyranyl, 4'-methoxytetrahydrothiopyranyl S,S-dioxido, tetrahydrofuranyl, tetrahydrothiofuranyl, 1-ethoxyethyl, 1-methyl-1-methoxyethyl, 1-(isopropoxy)ethyl, tri(p-methoxyphenyl)methyl, di(p-methoxy)phenylmethyl, 2,2,2-trichloroethyl, 2-(phenylselenyl)ethyl, butyl, allyl, cinnamyl, p-chlorophenyl, benzyl, p-methoxybenzyl, o-nitrobenzyl, p-nitrobenzyl, p-halobenzyl, p-cyanobenzyl, 3-methyl-2-picolyl N-oxido, diphenylmethyl, 5-dibenzosuberyl, triphenylmethyl, α-naphthyldiphenylmethyl, p-methoxyphenyldiphenylmethyl, p-(p'-bromophenacyloxy)phenyldiphenylmethyl, 9-anthryl, 9-(9-phenyl-10-oxo)anthryl, benzisothiazolyl S,S-dioxido, trimethylsilyl, triethylsilyl, isopropyldimethylsilyl, t-butyl dimethylsilyl, (triphenylmethyl)dimethylsilyl, methyldiiosopropylsilyl, methyl di-t-butylsilyl, tribenzylsilyl, tri-p-xylylsilyl, triisopropylsilyl and triphenylsilyl; B is a nucleotide base.

2. The mononucleoside 5'-triphosphate of claim 1, wherein $R_1$ is selected from the group consisting of bis(2-chloroethoxy)methyl, 4-methoxytetrahydropyranyl, tetrahydrofuranyl, 1-ethoxyethyl, tri(p-methoxyphenyl)methyl, di(p-methoxy)phenylmethyl and t-butyldimethylsilyl.

3. The mononucleoside 5'-triphosphate of claim 1, wherein $R_1$ is selected from the group consisting of methyl, $CH_3(CH_2)_N$, wherein N is an integer from 1–10, methoxymethyl, 2-methoxyethoxymethyl, trimethylsilyl and triethylsilyl.

4. The mononucleoside 5'-triphosphate of claim 1, wherein $R_1$ is a 1-ethoxyethyl group and said mononucleoside 5'-triphosphate is a deoxynucleoside.

5. The mononucleoside 5'-triphosphate of claim 1, wherein $R_1$ is a 1-ethoxyethyl group.

6. A mononucleoside 5'-triphosphate having a removable blocking moiety protecting the 3' position which is an ether and which has the following formula:

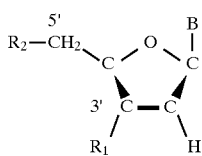

wherein $R_2$ is a triphosphate group; $R_1$ is a silyl group; and B is a nucleotide base.

* * * * *

UNITED STATES PATENT AND TRADEMARK OFFICE
CERTIFICATE OF CORRECTION

PATENT NO. : 5,872,244
DATED : February 16, 1999
INVENTOR(S) : Hiatt et al.

It is certified that error appears in the above-indentified patent and that said Letters Patent is hereby corrected as shown below:

Column 1, line 36, "if" should read --is--.
Column 1, line 67, after "formation" delete --,--.
Column 3, line 15, "3'" should read --3'--.
Column 5, line 21, "provided" should read --prepared--.
Column 5, line 25, after "proteins" insert --are also provided.--
Column 7, line 60, "having" should read --has--.
Column 9, line 65, after "invention" insert --which--.
Column 10, line 9, "R2" should read --$R_2$--.
Column 10, line 10, "R1" should read --$R_1$-.
Column 10, line 11, "R2" should read --$R_2$--.
Column 10, line 12 "R1" should read --$R_1$-.
Column 10, line 64, "R2" should read --$R_2$--.
Column 10, line 65 "R1" should read --$R_1$-.
Column 11, line 43, "R2" should read --$R_2$--.

Column 11, line 60 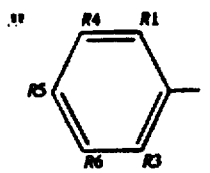

should read -- 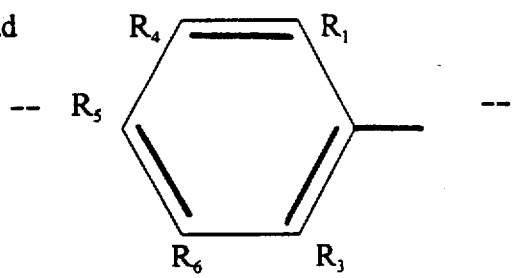 --

UNITED STATES PATENT AND TRADEMARK OFFICE
CERTIFICATE OF CORRECTION

PATENT NO. : 5,872,244

DATED : February 16, 1999

INVENTOR(S) : Hiatt et al.

It is certified that error appears in the above-indentified patent and that said Letters Patent is hereby corrected as shown below:

Column 11, line 62, "R1, R3, R4, R5 and R6" should read
-- $R_1$, $R_3$, $R_4$, $R_5$ and $R_6$ --

Column 12, lines 15-22, in the formula, "R1" should read --$R_1$--

Column 12, line 23, "R2" should read --$R_2$--

Column 12, line 24, "R1" should read --$R_1$--.
Column 12, lines 31-40, in the formula "R1" should read --$R_1$--.
Column 12, line 25, "unsubstituted:" should read --unsubstituted--.
Column 12, line 41, "R2" should read --$R_2$--.
Column 12, line 42, "R1" should read --$R_1$--.
Column 13, line 11, "R2" should read --$R_2$--
Column 13, lines 20-29, in the formula "R1" should read --$R_1$--.
Column 13, line 30, "R2" should read --$R_2$--.
Column 13, line 31, "R1" should read --$R_1$--.
Column 13, line 35, "R1" should read --$R_1$--.
Column 13, line 35, "R2" should read --$R_2$--
Column 13, line 58, "R2" should read --$R_2$--
Column 13, line 59, "R1" should read --$R_1$--
Column 13, line 62, "R2" should read --$R_2$--
Column 13, line 63, "R1" should read --$R_1$--
Column 14, lines 1-8, in the formula "R1" should read --$R_1$--.
Column 14, line 9, "R2" should read --$R_2$--.
Column 14, line 10, "R1" should read --$R_1$--.
Column 14, line 17, after "ester" insert --that--.
Column 22, line 43, "desire" should read --desired--.

UNITED STATES PATENT AND TRADEMARK OFFICE
CERTIFICATE OF CORRECTION

PATENT NO. : 5,872,244
DATED : February 16, 1999
INVENTOR(S) : Hiatt et al.

Page 3 of 4

It is certified that error appears in the above-indentified patent and that said Letters Patent is hereby corrected as shown below:

Column 23, line 61, "describe" should read --described--.
Column 24, line 17, after "above" insert --,--.
Column 27, line 64, "Rf" should read --$R_f$--.
Column 28, line 4, "10 MM" should read --10 mM--
Column 31, line 54, "1 MM" should read --1 mM--
Column 34, line 3, "reaction" should read --reactions--.
Column 37, lines 35-43,

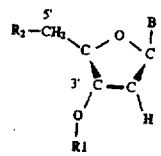

should read

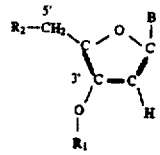

UNITED STATES PATENT AND TRADEMARK OFFICE
CERTIFICATE OF CORRECTION

PATENT NO. : 5,872,244
DATED : February 16, 1999
INVENTOR(S) : Hiatt et al.

It is certified that error appears in the above-indentified patent and that said Letters Patent is hereby corrected as shown below:

Column 38, lines 55-62

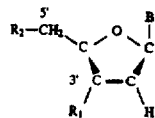

should read

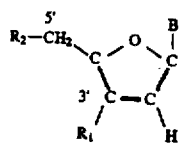

Signed and Sealed this

Fifth Day of October, 1999

Attest:

Q. TODD DICKINSON

Attesting Officer

Acting Commissioner of Patents and Trademarks

(12) EX PARTE REEXAMINATION CERTIFICATE (8584th)
United States Patent
Hiatt et al.

(10) Number: US 5,872,244 C1
(45) Certificate Issued: Oct. 4, 2011

(54) 3' PROTECTED NUCLEOTIDES FOR ENZYME CATALYZED TEMPLATE-INDEPENDENT CREATION OF PHOSPHODIESTER BONDS

(75) Inventors: Andrew C. Hiatt, San Diego, CA (US); Floyd Rose, Del Mar, CA (US)

(73) Assignee: Illumina, Inc., San Diego, CA (US)

Reexamination Request:
No. 90/009,767, Jul. 23, 2010

Reexamination Certificate for:
Patent No.: 5,872,244
Issued: Feb. 16, 1999
Appl. No.: 08/486,535
Filed: Jun. 7, 1995

Certificate of Correction issued Oct. 5, 1999.

Related U.S. Application Data

(63) Continuation-in-part of application No. 08/300,484, filed on Sep. 2, 1994, now Pat. No. 5,990,300.

(51) Int. Cl.
| | |
|---|---|
| C07H 19/00 | (2006.01) |
| C07H 19/10 | (2006.01) |
| C07H 19/20 | (2006.01) |
| C07H 21/00 | (2006.01) |
| C12P 19/30 | (2006.01) |
| C12P 19/00 | (2006.01) |

(52) U.S. Cl. .................... 536/26.26; 536/26.6; 536/26.7
(58) Field of Classification Search .................. None
See application file for complete search history.

(56) References Cited

U.S. PATENT DOCUMENTS

| | | |
|---|---|---|
| 4,711,955 A | 12/1987 | Ward et al. |
| 5,118,605 A | 6/1992 | Urdea |
| 5,302,509 A | 4/1994 | Cheeseman |
| 5,872,244 A | 2/1999 | Hiatt et al. |
| 6,214,987 B1 | 4/2001 | Hiatt et al. |
| 7,459,275 B2 | 12/2008 | Dower et al. |

FOREIGN PATENT DOCUMENTS

| | | |
|---|---|---|
| WO | 90/15070 | 12/1990 |
| WO | WO 91/06678 | 5/1991 |
| WO | 92/10587 | 6/1992 |
| WO | 2004/018497 | 3/2004 |

OTHER PUBLICATIONS

Gait, "Oligonucleotide Synthesis: A Practical Approach," IRL Press, Oxford, 225 pages (1984).

Chambers, et al., "Buffers, Chelating Agents And Denaturants," Biochemistry Labfax, Bios Scientific Publishers, pp. 1–11 (1993).

Scopes, Robert K., "Buffers For Use In Protein Chemistry," Protein Purification Principles and Practice, Third Edition, Springer–Velag, pp. 351–352 (1994).

New England Biolabs On–Line Catalog, "Taq DNA Polymerase with Standard Buffer(M0273), Routine PCR, NEB," New england Bio Labs Inc., http://www.neb.com/nebecomm/products/productm0273.asp, pp. 1–3 (2011 (printed Mar. 20, 2011)).

Losse, et al, "Der 2–Benzyloxycarbonyl–benzoyl–Rest als OH–Schutz für Depsipeptid–Synthesen," Chem. Ber., vol. 98, pp. 1522–1530 (1965), and English language Abstract thereof.

Reese, "Tetrahedron Report No. 56; The Chemical Synthesis Of Oligo– and Poly–Nucleotides By The Phosphotriester Approach," Tetrahedron, vol. 34, pp. 3144–3179 (1978).

Büchi et al., "CV. Total Synthesis Of The Structural Gene For An Alanine Transfer Ribonucleic Acid From Yeast. Chemical Synthesis Of An Icosadeoxyribonucleotide Corresponding To The Nucleotide Sequence 31 to 50," J. Mol Biol., vol. 72, pp. 251–288 (1972).

Watanabe, et al., "Synthesis of a Lividomycin B Analogue, 5–0–[3–0–(2–Amino–2–deoxy–α–D–glucopyranosyl)–β–D–ribofuranosyl]–3'–deoxyparomamine ," Bulletin of the Chemical Society of Japan, vol. 50 (9), pp. 2369–2374 (1977).

Cook et al., "Use of Chloroacetic Anhydride for the Protection of Nuceoside Hydroxyl Groups," J. Org. Chem., vol. 35, No. 6, pp. 1940–1943 (1970).

Kupchan et al., "The Tiglate Ester as an Alcohol Blocking Group in Organic Synthesis," J. Org. Chem., vol. 27, pp. 3103–3106 (1962).

Wuts and Greene, Greene's Protective Groups in Organic Synthesis, 2nd Ed., 1991, John Wiley & Sons, New York, p. 10–14 and Chapter 2 ("Ethers") beginning on p. 14.

Kraevskii et al., Molecular Biology 21:25–29 (1987), entire document.

Kutateladze et al., FEBS Letters 207(2): 205–212 (1986), entire document.

Axelrod et al., Nucleic Acids Research 5(10): 3549–3583 (1978), entire document.

(Continued)

*Primary Examiner* — Bruce Campell

(57) ABSTRACT

A method for the stepwise creation of phosphodiester bonds between desired nucleosides resulting in the synthesis of polynucleotides having a predetermined nucleotide sequence by preparing an initiation substrate containing a free and unmodified 3'-hydroxyl group; attaching a mononucleotide selected according to the order of the predetermined nucleotide sequence to the 3'-hydroxyl of the initiating substrate in a solution containing a catalytic amount of an enzyme capable of catalyzing the 5' to 3' phosphodiester linkage of the 5'-phosphate of the mononucleotide to the 3'-hydroxyl of the initiating substrate, wherein the mononucleotide contains a protected 3'-hydroxyl group, whereby the protected mononucleotide is covalently linked to the initiating substrate and further additions are hindered by the 3'-hydroxyl protecting group. Methods in which a mononucleotide immobilized on a solid support is added to a free polynucleotide chain are also disclosed.

OTHER PUBLICATIONS

Amit et al., "Photosensitive Protecting Groups of Amino Sugars and Their Use in Glycoside Synthesis. 2–Nitrobenzyloxycarbonylamino and Nitroveratryloxycarbonylamino Derivatives," Journal of Organic Chemistry, vol. 39, No. 2, pp. 192–196 (1974).

Cantoni et al., "Characterization of DNA Lesions Produced by HgCl2 in Cell Culture Systems," Chemico–Biological Interactions, vol. 49, pp. 209–224 (1984).

Cantoni et al., "Mechanism of HgCI2 Cytotoxicity in Cultured Mammalian Cells," Molecular Pharmacology, vol. 26, pp. 360–368 (1984).

Chinault et al., "Preparation of *Escherichia coli* tRNAs Terminating in Modified Nucleosides by the Use of CTP (ATP):tRNA Nucleotidyltransferase and Polynucleotide Phosphorylase," Biochemistry, vol. 16, No. 4, pp. 756–765 (1977).

Costa et al., "DNA Damage by Mercury Compounds: An Overview," In Advances in Mercury Toxicology, pp. 255–273 Plenum Press New York (1991).

Dale et al., "Conversion of Covalently Mercurated Nucleic Acids to Tritiated and Halogenated Derivatives," Nucleic Acids Research, vol. 2, No. 6, pp. 915–930 (1975).

Dale, et al., "The Synthesis and Enzymatic Polymerization of Nucleotides Containing Mercury: Potential Tools for Nucleic Acid Sequencing and Structural Analysis," Proceedings of the National Academy of Science USA vol. 70, No. 8, pp. 2238–2242 (1973).

Eichhorn et al., "The Reaction of Mercury (II) with Nucleosides," Journal of the American Chemical Society, vol. 85, No. 24, pp. 4020–4024 (1963).

Gait, "Oligonucleotide Synthesis: A Practical Approach," IRL Press, Oxford, p. 5 (1984).

Gigg et al., "The Allyl Ether as a Protecting Group in Carbohydrate Chemistry," Part II, Journal Chemical Society, pp. 1903–1911 (1968).

Gruenwedel et al., "Mercury–Induced DNA Polymorphism: Probing the Conformation of Hg(II)–DNA via Staphylococcal Nuclease Digestion and Circular Dichroism Measurements," Biochemistry, vol. 29, No. 8, pp. 2111–2116 (1989).

Hayakawa et al., "O–Allyl Protection of Guanine and Thymine Residues in Oligodeoxyribonucleotides," Journal of Organic Chemistry, vol. 58, pp. 5551–5555 (1993).

Henner et al., "Enzyme Action at 3' Termini of Ionizing Radiation–induced DNA Strand Breaks," The Journal of Biological Chemistry, vol. 258, No. 24, pp. 15198–15205 (1983).

Honda et al., "Deprotection of Allyl Groups with Sulfinic Acids and Palladium Catalyst," Journal of Organic Chemistry, vol. 62 pp. 8932–8936 (1997).

Hovinen, et al., "Synthesis of 3'–0–(ω–Aminoalkoxymethyl)thymidine 5'–Triphosphates, Terminators of DNA Synthesis that Enable 3'–Labeling," Journal Chemical Society Perkins Trans., Issue 2, pp. 211–217 (1994).

Ju et al., "Four–Color DNA Sequencing by Synthesis Using Cleavable Florescent Nuceotide Reversible Terminators," PNAS, vol. 103, No. 52, pp. 19635–19640 (2006).

Karakawa et al., "The Utility of a 3–0–Allyl Group as a Protective Group for Ring–Opening Polymerization of α–D–Glucopyranose 1 ,2,4–Orthopivalate Derivatives," Biomacromolecules, voll 3, pp. 538–546 (200).

Katz, "The Reversible Reaction of Sodium Thymonucleate and Mercuric Chloride," Journal of the American Chemical Society, vol. 74, No. 9, pp. 2238–2245 (1952).

Kruse et al., "Use of (Thio)Acetal Esters as Reagents for the Protection of Alcohols Synthesis of 2– Tetrahvdrothienvl Ethers," Journal of Organic Chemistry, pp. 43, No. 18, pp. 3548–3553 (1978).

Letsinger et al., "2,4–Dinitrobenzenesulfenyl as a Blocking Group for Hydroxyl Functions in Nucleotides," Journal of American Chemistry, vol. 29, pp. 2615–2618 (1964).

Matsuoka et al., "Mercury Chloride Activates c–Jun N–Terminal Kinase and Induces c–jun Expression in LLC–PK1 Cells," Toxicological Sciences, vol. 53, pp. 361–368 (2000).

Metzker, "Emerging Technologies in DNA Sequencing;" Genome Research, vol. 15, pp. 1767–1776 (2005).

Patchornik, et al., "Photosensitive Protecting Groups," Journal of American Chemical Society, vol. 92, No. 21, pp. 63333–6335 (1970).

Prober et al., "A System for Rapid DNA Sequencing with Fluorescent Chain–Terminating Dideoxynucleotides," Science, vol. 238, pp. 336–341 (1987).

Ruparel et al., "Design and Synthesis of a 3'–0–allyl Photocleavable Fluorescent Nucleotide as a Reversible Terminator for DNA Sequencing by Synthesis," PNAS, vol. 102, No. 17, pp. 5932–5937 (2005).

Welch et al, "Syntheses of Nucleosides Designed for Combinatorial DNA Sequencing," European Journal of Organic Chemistry, vol. 5, No. 3, pp. 951–960 (1999).

Yamane, "On the Complexing of Desoxyribonucleic Acid (DNA) by Mercuric Ion," Journal of the American Chemical Society, vol. 83, No. 12, pp. 2599–2607 (1961).

Young et al., "Binding of Mercury(II) to Poly(dA–dT) Studied by Proton Nuclear Magnetic Resonance," Biochemistry, vol. 21, pp. 62–66 (1982).

Corrected Third Party Request for Ex Parte Reexamination filed Jul. 23, 2010, in Reexamination Control No. 90/009, 769.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claim 6 is confirmed.

Claims 1 and 3 are determined to be patentable as amended.

Claims 2, 4 and 5, dependent on an amended claim, are determined to be patentable.

New claims 7-9 are added and determined to be patentable.

1. A mononucleoside 5'-triphosphate having a removable blocking moiety protecting the 3' position which is an ether and which has the following formula:

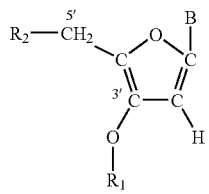

wherein $R_2$ is a triphosphate group and $R_1$ is selected from the group consisting of [methyl, $CH_3$ $(CH_2)_N$] $CH_3(CH_2)_N$, wherein N is an integer from 1-10, methoxymethyl, methylthiomethyl, benzyloxymethyl, t-butyoxymethyl, 2-methoxyethoxymethyl, 2,2,2-trichloroethoxymethyl, bis(2-chloroethoxy)methyl, 2-(trimethylsilyl)ethoxymethyl, tetrahydropyranyl, 3'-bromotetrahydropyranyl, tetrahydrothiopyranyl, 4'-methoxytetrahydropyanyl, 4'-methoxytetrahydrothiopyranyl, 4'-methoxytetrahydrothiopyranyl S,S-dioxido, tetrahydrofuranyl, tetrahydrothiofuranyl, 1-ethoxyethyl, 1-methyl-1-methoxyethyl, 1-(isopropoxy)ethyl, tri(p-methoxyphenyl)methyl, di(p-methoxy)phenylmethyl, 2,2,2-trichloroethyl, 2-(phenylselenyl)ethyl, butyl, allyl, cinnamyl, p-chlorophenyl, benzyl, p-methoxybenzyl, o-nitrobenzyl, p-nitrobenzyl, p-halobenzyl, p-cyanobenzyl, 3-methyl-2-picolyl N-oxide, diphenylmethyl, 5-dibenzosuberyl, triphenylmethyl, α-naphthyldiphenylmethyl, p-methoxyphenyldiphenylmethyl, p-(p'-bromophenacyloxy)phenyldiphenylmethyl, 9-anthryl, 9-(9-phenyl-10-oxo)anthryl, benzisothiazolyl S,S-dioxido, trimethylsilyl, triethylsilyl, isopropyldimethylsilyl, t-butyl dimethylsilyl, (triphenylmethyl)dimethylsilyl, methyldiisopropylsilyl, methyl di-t-butylsilyl, tribenzylsilyl, tri-p-xylylsilyl, triisopropylsilyl and triphenylsilyl; B is a nucleotide base.

3. The mononucleoside 5'-triphosphate of claim 1, wherein $R_1$ is selected from the group consisting of [methyl, $CH_3$ $(CH_2)_N$] $CH_3(CH_2)_N$, wherein N is an integer from 1-10, methoxymethyl, 2-methoxyethoxymethyl, trimethylsilyl and triethylsilyl.

*7. A mononucleoside 5'-triphosphate having a removable blocking moiety protecting the 3' position which is an ether and which has the following formula:*

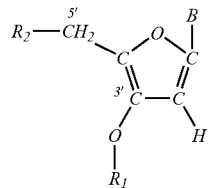

*wherein $R_2$ is a triphosphate group and $R_1$ is selected from the group consisting of methylthiomethyl, benzyloxymethyl, t-butyoxymethyl, 2-methoxyethoxymethyl, 2,2,2-trichloroethoxymethyl, bis(2-chloroethoxy)methyl, 2-(trimethylsily)ethoxymethyl, tetrahydropyranyl, 3'-bromotetrahydropyranyl, tetrahydrothiopyranyl, 4'-methoxytetrahydropyranyl, 4'-methoxytetrahydrothiopyrnyl, 4'-methoxytetrahydrothiopyranyl S,S-dioxido, 1-ethoxyethyl, 1-methyl-1-methoxyethyl, 1-(isopropoxy)ethyl, tri(p-methoxyphenyl)methyl, di(p-methoxy)phenylmethyl, 2,2,2-trichloroethyl, 2-(phenylselenyl)ethyl, butyl, cinnamyl, benzyl, p-chlorophenyl, p-methoxybenzyl, p-halobenzyl, p-cyanobenzyl, 3-methyl-2-picolyl N-oxido, diphenylmethyl, 5-dibenzosuberyl, triphenylmethyl, α-naphthyldiphenylmethyl, p-methoxyphenyldiphenylmethyl, p-(p'-bromophenacyloxy)phenyldiphenylmethyl, 9-anthryl, 9-(9-phenyl-10-oxo)anthryl, benzisothiazolyl S,S-dioxido, trimethylsilyl, triethylsilyl, isopropyldimethylsilyl, (triphenylmethyl)dimethylsilyl, methyldiiosopropylsilyl, methyl di-t-butylsilyl, tribenzylsilyl, tri-p-xylylsilyl, triisopropylsilyl and triphenylsilyl; B is a nucleotide base.*

*8. The mononucleoside 5'-triphosphate of claim 7, wherein $R_1$ is selected from the group consisting of bis(2-chloroethoxy)methyl, 4-methoxytetrahydropyranyl, 1-ethoxyethyl, tri(p-methoxyphenyl)methyl, di(p-methoxy)phenylmethyl and t-butyldimethylsilyl.*

*9. The mononucleoside 5'-triphosphate of claim 7, wherein $R_1$ is selected from the group consisting of 2-methoxyethoxymethyl, trimethylsilyl and triethylsilyl.*

* * * * *